US010724009B2

(12) United States Patent
Page et al.

(10) Patent No.: US 10,724,009 B2
(45) Date of Patent: Jul. 28, 2020

(54) CANNABICHROMENIC ACID SYNTHASE FROM *CANNABIS SATIVA*

(71) Applicant: NATIONAL RESEARCH COUNCIL OF CANADA (NRC), Ottawa (CA)

(72) Inventors: Jonathan E. Page, Vancouver (CA); Jason M. Stout, Winnipeg (CA)

(73) Assignee: National Research Council of Canada (NRC), Ottawa (CA)

(*) Notice: Subject to any disclaimer, the term of this patent is extended or adjusted under 35 U.S.C. 154(b) by 0 days.

(21) Appl. No.: 16/443,217

(22) Filed: Jun. 17, 2019

(65) Prior Publication Data

US 2019/0382734 A1 Dec. 19, 2019

Related U.S. Application Data

(63) Continuation of application No. 15/321,585, filed as application No. PCT/CA2015/000423 on Jun. 29, 2015, now Pat. No. 10,364,416.

(60) Provisional application No. 62/018,128, filed on Jun. 27, 2014.

(51) Int. Cl.
| | |
|---|---|
| C12N 1/20 | (2006.01) |
| C12N 9/02 | (2006.01) |
| C12P 17/06 | (2006.01) |
| C12N 15/82 | (2006.01) |
| C07K 16/40 | (2006.01) |
| C12N 15/52 | (2006.01) |

(52) U.S. Cl.
CPC .............. *C12N 9/001* (2013.01); *C07K 16/40* (2013.01); *C12N 15/52* (2013.01); *C12N 15/8243* (2013.01); *C12P 17/06* (2013.01); *C12Y 103/03* (2013.01)

(58) Field of Classification Search
CPC .................................. C12N 15/52; C07K 16/40
See application file for complete search history.

(56) References Cited

U.S. PATENT DOCUMENTS

| | | |
|---|---|---|
| 7,112,717 B2 | 9/2006 | Valentin et al. |
| 8,884,100 B2 | 11/2014 | Page |
| 9,765,308 B2 | 9/2017 | Page et al. |
| 2003/0180945 A1 | 9/2003 | Wang |
| 2006/0035236 A1 | 2/2006 | Keim et al. |
| 2012/0144523 A1 | 6/2012 | Page |
| 2013/0067619 A1 | 3/2013 | Page |
| 2013/0267429 A1 | 10/2013 | Gardner et al. |
| 2014/0057251 A1 | 2/2014 | McKernan |
| 2014/0141476 A1 | 5/2014 | Page |
| 2016/0177404 A1 | 6/2016 | McKernan |

FOREIGN PATENT DOCUMENTS

| | | |
|---|---|---|
| JP | 2000078979 A | 3/2000 |
| JP | 2001029082 A1 | 2/2001 |
| JP | 2007020466 A | 2/2007 |
| WO | 9824929 A1 | 6/1998 |
| WO | 2011017798 A1 | 2/2011 |
| WO | 2011/127589 A1 | 10/2011 |
| WO | 2013/006953 A1 | 1/2013 |

OTHER PUBLICATIONS

Stout, J. M., et al., The hexanoyl-CoA precursor for cannabinoid biosynthesis is formed by an acyl-activating enzyme in *Cannabis sativa* trichomes. Plant J. (2012) 71(3): 353-65.
Taura F, et al., Purification and characterization of cannabidiolic-acid synthase from *Cannabis sativa* L. Biochemical analysis of a novel enzyme that catalyzes the oxidocyclization of cannabigerolic acid to cannabidiolic acid. J Biol Chem. (1996) 271: 17411-17416.
Taura F, et al., First direct evidence for the mechanism of 1-tetrahydrocannabinolic acid biosynthesis. Journal of the American Chemical Society (1995) 117: 9766-9767.
Taura F, et al., Cannabidiolic-acid synthase, the chemotype-determining enzyme in the fiber-type *Cannabis sativa*. FEBS Left. (2007) 581: 2929-2934.
Taura F, et al., Characterization of olivetol synthase, a polyketide synthase putatively involved in cannabinoid biosynthetic pathway. FEBS Lett. (2009) 583: 2061-2066.
Vasil I K, Molecular improvement of cereals. Plant Mol. Biol. (1994) 25: 925-937.
Walden R, et al., Gene-transfer and plant regeneration techniques. Trends in Biotechnology (1995) 13: 324-331.
Zhang, H. et al., Bacterial hosts for natural product production. Mol. Pharmaceutics (2008), 5(2) 212-225.
Maione, S. et al., Non-psychoactive cannabinoids modulate the descending pathway of antinociception in anaesthetized rats through several mechanisms of action. British Journal of Pharmacology (2011) 162(3), 584-96.
Marks, MD. et al., Identification of candidate genes affecting Delta9-tetrahydrocannabinol biosynthesis in *Cannabis sativa*. J Exp Bot. (2009) 60, 3715-3726.
Ware, M.A. et al., Smoked cannabis for chronic neuropathic pain: a randomized controlled trial. Canadian Medical Association Journal (2010) 182(14), E694-701.
Puigbo et al., 2007, Nuc. Acid. Res., 35:W126-W131.
Marks M D et al. *Cannabis sativa* (marijuana cultivar Skunk #1) glandular trichomes isolated from female inflorescences *Cannabis sativa* cDNA, mRNA sequence. GenBank Accession GR221141, 2005.
Boubakir, Z. et al., An aromatic prenyltransferase involved in cannabinoid biosynthesis from *Cannabis sativa*. Banff Conference on Plant Metabolism (2010) Jun. 24-28, 2010, abstract CS6 only.
Veress, T. et al., Determination of cannabinoid acids by high performance liquied chromatography of their neutral derivatives formed by thermal decarboxylation. Journal of Chromatography (1990) 520:339-347.

(Continued)

*Primary Examiner* — Tekchand Saidha

(74) *Attorney, Agent, or Firm* — Carmela De Luca; Bereskin & Parr LLP

(57) ABSTRACT

Nucleic acid molecules from cannabis have been isolated and characterized and encode polypeptides having cannabichromenic acid synthase activity. Expression or over-expression of the nucleic acids alters levels of cannabinoid compounds. The polypeptides may be used in vivo or in vitro to produce cannabinoid compounds.

28 Claims, 4 Drawing Sheets

Specification includes a Sequence Listing.

(56) References Cited

OTHER PUBLICATIONS

Katsuyama Yohei, Synthesis of Unnatural Flavonoids and Stilbenes by Exploiting the Plant Biosynthetic Pathway in *Escherichia coli*, Chemistry & Biology 14, 613-621, Jun. 2007.
International Preliminary Examination Report dated Oct. 16, 2012 based on PCT/CA2011/000428.
International Search Report dated Jul. 29, 2011 based on PCT/CA2011/000428.
Written Opinion dated Jul. 29, 2011 based on PCT/CA2011/000428.
Earley, K.W. et al. Gateway-compatible vectors for plant functional genomics and proteomics. Plant J. 45, 616-629, 2006.
Li X. et al. Deleteagene: a fast neutron deletion mutagenesis-based gene knockout system for plants. Comp Funct Genomics. 3: 158-60, 2002.
Nelson, B.K. et al. A multicolored set of in vivo organelle markers for co-localization studies in *Arabidopsis* and other plants. Plant J. 51, 1126-1136, 2007.
Shockey J. and Browse J. Genome-level and biochemical diversity of the acyl-activating enzyme superfamily in plants. The Plant Journal 66:143-60, 2011.
Fernandez-Valverde M. et al. Use of long-chain fatty acid-CoA ligase (AMP-forming) from Pseudomonas fragi for the "in vitro" synthesis of natural penicillins. FEMS Microbiology Letters 96:111-114, 1992 (abstract only).
Chan A. et al. GenBank Accession No. XM_002511961, Aug. 6, 2009. Ricinus communis acetyl-CoA synthetase, putative, mRNA. Retrieved on Aug. 7, 2012 from GenBank Accession No. XM_002511961, version XM_002511961.1 gi:255541885 <http://www.ncbi.nlm.nih.gov/nucleotide/XM_002511961>.
Beuning L. et al. GenBank Accession No. ES790087, Jun. 26, 2007. 061124AALA001303CT (AALA) Royal Gala 150 DAFB fruit cortex Malus x domestica cDNA clone AALAA00130, mRNA sequence. Retrieved on Oct. 4, 2012 from GenBank Accession No. ES790087, version ES790087 GI: 149780311 <http://www.ncbi.nlm.nih.gov/nucest/ES790087>.
Watson et al., RNA Silencing Platforms in Plants. Article in Press. Aug. 2005. 1-6.
Jackson et al., Expression profiling reveals off-target gene regulation by RNAi. 2003 Nature Biotechnology. 1-3.
Niggeweg, et al. Engineering plants with increased levels of the antioxidant chlorogenic acid. Nature Biotechnology. vol. 22, No. 6, Jun. 2004, 746-754.
Alvarez JP, Pekker I, Goldshmidt A, Blum E, Amsellem Z, Eshed Y (2006) Endogenous and Synthetic MicroRNAs Stimulate Simultaneous, Efficient, and Localized Regulation of Multiple Targets in Diverse Species. Plant Cell 18:1134-51.
Lithwick G, Margalit H (2003) Hierarchy of sequence-dependent features associated with prokaryotic translation. Genome Research 13: 2665-73.
Marks MD, Tian L, Wenger JP, Omburo SN, Soto-Fuentes W, He J, Gang DR, Weiblen GD, Dixon RA. (2009) Identification of candidate genes affecting Delta9-tetrahydrocannabinol biosynthesis in *Cannabis sativa*. J Exp Bot. 60, 3715-3726.
Needleman and Wunsch, J. Mol. Biol. 48: 443 (1970).
Pearson and Lipman, Proc. Natl. Acad. Sci. (U.S.A.) 85: 2444 (1988).
Smith and Waterman, Ad. App. Math 2: 482-489 (1981).
Marks et al, 2009, J Exp. Botany, 60: 3715-3726, Supp Table 1 and Supp Table 2.
Laverty et al (2019) A physical and genetic map of *Cannabis sativa* identifies extensive rearrangements at the THC/CBD acid synthase loci. Genome Res. 29(1):146-156.
Morimoto et al. Purification and characterization of cannabichromenic acid synthase from *Cannabis sativa*. Phytochemistry vol. 49, No. 6, pp. 1525-1529, 1998.
Meijer et al. The inheritance of chemical phenotype in *Cannabis saliva* L. (IV): cannabinoid-free plants. Euphytica (2009) 168:95-112.

Meijer et al. Hie Inheritance of Chemical Phenotype in *Cannabis saliva* L. Genetics I63; 335-346 (Jan. 2003).
Pakula A.A, Sauer R.T., Genetic analysis of protein stability and functions, Annual Review of Genetics, 1989, vol. 23, pp. 289-310.
Kojoma, M. et al., DNA polymorphisms in the tetrahydrocannabinolic acid (THCA) synthase gene in "drug-type" and "fiber-type" *Cannabis sativa* L. Forensic Science International 159 (2006) 132-140.
Alvarez, JP. et al., Endogenous and synthetic microRNAs stimulate simultaneous, efficient, and localized regulation of multiple targets in diverse species. Plant Cell (2006) 18:1134-51.
Van Bakel, H. et al., The draft genome and transcriptome of *Cannabis sativa*. Genome Biology (2011) 12(10), R102: 1-17.
Bechtold N. et al., In planta Agrobacterium-mediated gene transfer by infiltration of adult *Arabidopsis thaliana* plants. C R Acad Sci Paris, Sciences de la vie/Life sciences (1993) 316: 1194-1199.
Becker D. et al., Fertile transgenic wheat from microprojectile bombardment of scutellar tissue. Plant J.(1994) 5: 299-307.
Lytle et al. Letter to the Editor: Structure of the hypothetical protein At3g17210 from *Arabidopsis thaliana*. Journal of Biomolecular NMR 28: 397-400, 2004.
Collakova E, et al., Isolation and functional analysis of homogentisate phytyltransferase from *Synechocystis* sp. PCC 6803 and *Arabidopsis*. Plant Physiol (2011) 127: 1113-1124.
Datla R. et al., Plant promoters for transgene expression. Biotechnology Annual Review (1997) 3: 269-296.
Davis, W. M. et al., Neurobehavioral actions of cannabichromene and interactions with delta 9-tetrahydrocannabinol. General Pharmacology (1983) 14(2), 247-52.
Deblock M. et al., Transformation of *Brassica napus* and *Brassica oleracea* using Agrobacterium tumefaciens and the expression of the bar and neo genet; in the transgenic plants. Plant Physiol. (1989) 91: 694-701.
Delong, G. T. et al., Pharmacological evaluation of the natural constituent of *Cannabis sativa*, cannabichromene and its modulation by 0(9)-tetrahydrocannobinol. Drug and Alcohol Dependence (2010) 112(1-2), 126-33.
Depicker A. et al., Post-transcriptional gene silencing in plants. Curr Opin Cell Biol.(1997) 9: 373-82.
Elsohly, M. A., et al., Chemical constituents of marijuana: the complex mixture of natural cannabinoids. Life Sciences (2005) 78(5) 539-48.
Feeney M. et al., Tissue culture and Agrobacterium-mediated transformation of Hemp (*Cannabis sativa* L.) In Vitro Cell Dev Biol-Plant (2003) 39:578-585.
Fellermeier M. et al., Prenylation of olivetolate by a hemp transferase yields cannabigerolic acid, the precursor of tetrahydrocannabinol. FEBS Letters (1998) 427: 283-285.
Fernandez-Valverde, M. et al., Purification of Pseudomonas putida acyl coenzyme A ligase active with a range of aliphatic and aromatic substrates. Appl. Envir. Microbiol. (1993) 59(4), 1149-1154.
Gagne, S. et al., Identification of olivetolic acid cyclase from *Cannabis sativa* reveals a unique catalytic route to plant polyketides. Proceedings of the National Academy of Sciences of the United States of America (2012) 109(31), 12811-6.
Helliwell CA. et al., Constructs and methods for hairpin RNA-mediated gene silencing in plants. Methods Enzymology (2005) 392:24-35.
Izzo, A. A. et al., Inhibitory effect of cannabichromene, a major non-psychotropic cannabinoid extracted from *Cannabis sativa*, on inflammation-induced hypermotility in mice. British Journal of Pharmacology (2012) 166(4), 1444-60.
Henikoff S. et al., Tilling. Traditional mutagenesis meets functional genomics. Plant Physiol (2004) 135:630-6.
Katavic V. et al. In planta transformation of *Arabidopsis thaliana*. Mol. Gen. Genet. (1994) 245: 363-370.
Sparkes, Imogen A. et al. Rapid, transient expression of fluorescent fusion proteins in tobacco plants and generation of stably transformed plants. Nature Protocols, vol. 1, No. 4, pp. 21019-22025, 2006.
Leonard, E. et al., Strain Improvement of Recombinant *Escherichia coli* for Efficient Production of Plant Flavonoids. Mol Pharm. (2008).

(56) References Cited

OTHER PUBLICATIONS

Ligresti, A. et al., Antitumor activity of plant cannabinoids with emphasis on the effect of cannabidiol on human breast carcinoma. Journal of Pharmacology and Experimental Therapeutics (2006) 318(3), 1375-87.
Meyer, P., Understanding and controlling transgene expression. Trends in Biotechnology (1995) 13: 332-337.
Moloney, MM. et al., High efficiency transformation of *Brassica napus* using Agrobacterium vectors. Plant Cell Rep. (1989) 8: 238-242.
Morimoto, S. et al., Purification and characterization of cannabichromenic acid synthase from *Cannabis sativa*. Phytochemistry (1998) 49: 1525-1529.
Nehra, NS. et al.,Self-fertile transgenic wheat plants regenerated from isolated scutellar tissues following microprojectile bombardment with two distinct gene constructs. Plant J. (1994) 5: 285-297.
Ohyanagi, H. et al. The Rice Annotation Project Database (RAP-DB): hub for *Oryza sativa* ssp. *japonica* genome information. GenBank Accession NP_001060083, 2008.
Page, JE. et al., Biosynthesis of terpenophenolics in hop and cannabis. In JT Romeo, ed, Integrative Plant Biochemistry (2006) vol. 40. Elsevier, Oxford , pp. 179-210.
R. G. Pertwee, Cannabinoids R. G. Pertwee, Ed. (Springer-Verlag, Berlin/Heidelberg, 2005), pp. 1-51.
Ware, M. A., et al., Smoked cannabis for chronic neuropathic pain: a randomized controlled trial. CMAJ: Canadian Medical Association Journal = Journal de l'Association Medicale Canadienne (2010) 182(14), E694-701.
Potrykus, I., Gene transfer to plants: Assessment of published approaches and results. Annu. Rev. Plant Physiol. Plant Mol. Biol.(1991) 42: 205-225.
Taura, 2004, NISR Research Grant, 94-95.
Ralston, L. et al., Partial reconstruction of flavonoid and isoflavonoid biosynthesis in yeast using soybean type I and type II chalcone isomerases. Plant Physiol. (2005) 137(4): 1375-88.
Rhodes, CA. et al., Genetically transformed maize plants from protoplasts. Science (1988) 240: 204-207.
Romano, B. et al., The cannabinoid TRPA1 agonist cannabichromene inhibits nitric oxide production in macrophages and ameliorates murine colitis. British Journal of Pharmacology (2013) 169(1), 213-29.
Welch et al. (2009) Design parameters to control synthetic gene expression in *Escherichia coli*. PLoS ONE 4: e7002.
Sanford JC. et al., Delivery of substances into cells and tissues using a particle bombardment process. J. Part. Sci. Techno. (1987) 5: 27-37.
Schneider, K. et al., A new type of peroxisomal acyl-coenzyme A synthetase from *Arabidopsis thaliana* Has the Catalytic Capacity to Activate Biosynthetic Precursors of Jasmonic Acid. Journal of Biological Chemistry (2005) 280 (14), 13962-13972.
Schwab R, et al., Highly specific gene silencing by artificial microRNAs in *Arabidopsis*. Plant Cell (2006) 18:1121-33.
Shimamoto K, et al., Fertile transgenic rice plants regenerated from transformed protoplasts. Nature (1989) 338: 274-276.
Wirth, P. W., et al., Anti-inflammatory activity of cannabichromene homologs. Journal of Pharmaceutical Sciences, (1980) 69(11), 1359-60.
Shockey, J. M., et al., *Arabidopsis* Contains a Large Superfamily of Acyl-Activating Enzymes . Phylogenetic and Acyl-Coenzyme A Synthetases. Plant Physiol. (2003) 132(June), 1065-1076.
Shoyama Y, et al., Biosynthesis of propyl cannabinoid acid and its biosynthetic relationship with pentyl and methyl cannabinoid acids. Phytochemistry(1984) 23(9): 1909-1912.
Sirikantaramas S, et al., The gene controlling marijuana psychoactivity: molecular cloning and heterologous expression of Deltaltetrahydrocannabinolic acid synthase from *Cannabis sativa* L. J Biol Chem. (2004) 279: 39767-39774.
Sirikantaramas S, et al., Tetrahydrocannabinolic acid synthase, the enzyme controlling marijuana psychoactivity, is secreted into the storage cavity of the glandular trichomes. Plant Cell Physiol. (2005) 46: 1578-1582.
Songstad DD, et al., Advances in alternative DNA delivery techniques. Plant Cell, Tissue and Organ Culture (1995) 40:1-15.
Stam M, et al., Distinct features of post-transcriptional gene silencing by antisense transgenes in single copy and inverted T-DNA repeat loci. Plant J. (2000) 21:27-42.

US 10,724,009 B2

CANNABICHROMENIC ACID SYNTHASE FROM *CANNABIS SATIVA*

RELATED APPLICATIONS

This application is a Continuation Application of U.S. application Ser. No. 15/321,585, filed Dec. 22, 2016, which is a national phase entry of PCT/CA2015/000423, filed Jun. 29, 2015, which claims the benefit of priority of U.S. Provisional Patent Application No. 62/018,128, filed Jun. 27, 2014, each of these applications being incorporated herein in their entirety by reference.

INCORPORATION OF SEQUENCE LISTING

A computer readable form of the Sequence Listing "27119-P46298US02_SL.txt" (21,372 bytes), submitted via EFS-WEB and amended on Jun. 13, 2019, is herein incorporated by reference.

FIELD

The present disclosure relates to cannabichromenic acid synthase (CBCAS) enzyme from cannabis, a nucleotide sequence encoding the enzyme CBCAS based reagents, and methods for producing cannabinoids and/or altering cannabinoid production.

Introduction

*Cannabis sativa* L. (cannabis, hemp, marijuana) is one of the oldest and most versatile domesticated plants, which today finds use as source of medicinal, food, cosmetic and industrial products. It is also well known for its use as an illicit drug owing to its content of psychoactive cannabinoids (e.g. $\Delta^9$-tetrahydrocannabinol, THC). Plant-derived cannabinoids and other drugs that act through mammalian cannabinoid receptors are being explored as pharmaceutical drugs and/or used for the treatment of diverse conditions such as chronic pain, neuropathic pain in multiple sclerosis, anorexia, nausea, cancer/AIDS wasting and spasticity (Ware et al., 2010; Pertwee, 2005).

There are more than 80 cannabinoids known from cannabis (Elsohly and Slade, 2005). The major acidic cannabinoids are $\Delta^9$-tetrahydrocannabinolic acid (THCA), cannabidiolic acid (CBDA) and cannabichromenic acid (CBCA). Heat or prolonged storage leads to decarboxylation of the acidic cannabinoids (e.g. THCA forms THC, CBDA forms cannabidiol (CBD) and CBCA forms cannabichromene (CBC)).

The cannabinoid biosynthetic pathway is increasingly understood at the molecular and enzymatic level. The first enzyme is hexanoyl-CoA synthetase (Stout et al., 2013). Hexanoyl-CoA is used as a substrate for a reaction involving two enzymes, tetraketide synthase and olivetolic acid cyclase, which function together to synthesize olivetolic acid (Gagne et al, 2012). Olivetolic acid is geranylated by an aromatic prenyltransferase enzyme to form cannabigerolic acid (CBGA) (Fellermeier and Zenk, 1998), a branch-point intermediate that is converted by oxidocyclase enzymes to THCA, CBDA or CBCA. THCA synthase and CBDA synthase have been cloned and characterized (Sirikantaramas et al., 2005; Taura et al., 2007). The gene encoding CBCA synthase has not been reported.

The *Cannabis sativa* genome sequence was reported in van Bakel et al. (2011). However no sequence was identified for CBCA synthase.

Genetic evidence suggests that although THCA synthase and CBDA synthases may be allelic at the same locus, CBCA synthase is unlinked from these other enzymes (de Meijer et al., 2009, de Meijer et al., 2003).

Kojoma et al (2006) reported DNA polymorphisms in the THCA synthase gene in "drug type" and "fiber type" *Cannabis sativa*.

Cannabinoids are valuable plant-derived natural products. Genes encoding enzymes of cannabinoid biosynthesis will be useful in metabolic engineering of cannabis varieties that contain ultra-low levels of THC and other cannabinoids. Such genes may also prove useful for creation of specific cannabis varieties for the production of cannabinoid-based pharmaceuticals, production of enzymes catalyzing steps in formation of cannabinoids, or for reconstituting cannabinoid biosynthesis in other organisms such as bacteria or yeast.

SUMMARY

In an aspect, there is provided an isolated and/or purified nucleic acid molecule comprising: i) a nucleotide sequence having at least, greater than or about 96% sequence identity to SEQ ID NO: 1 or 5; ii) a nucleotide sequence having at least, greater than or about 78% sequence identity to SEQ ID NO: 1, 5 or 8 or 9 and encoding a polypeptide having cannabichromenic acid synthase activity; iii) the complement of i) or ii): or a fragment of greater than, at least or about 15 contiguous nucleotides of i), ii) or iii).

Also, in another aspect, primers and probes comprising nucleotide sequences having at least, greater than or about 96% sequence identity to a fragment of SEQ ID NO: 1, 5 or 8 or 9 or the complement thereof are provided.

Another aspect is a nucleic acid molecule encoding a polypeptide having at least, greater than or about 95% sequence identity to SEQ ID NO: 2 or 6, optionally with codon usage optimized for expression in an organism other than cannabis.

In an embodiment, the nucleic acid molecule comprises a nucleotide sequence having the sequence of SEQ ID NO: 1, 5, 8 or 9.

In another aspect, there is provided an isolated and/or purified polypeptide comprising an amino acid sequence having at least, greater than or about 95% sequence identity to SEQ ID NO: 2 or 6.

Also provided in another aspect is a nucleic acid molecule described herein linked to a heterologous signal sequence or tag. In an embodiment the nucleic acid molecule comprises a nucleotide sequence encoding a polypeptide having an amino acid sequence having at least, greater than or about 95% sequence identity to SEQ ID NO: 2 or 6 linked to a heterologous signal sequence or tag.

Also provided in another aspect is an antibody or binding fragment thereof that specifically binds an epitope of the amino acid sequence herein described in SEQ ID NO: 2 or 6 or a fragment thereof.

Another aspect includes a nucleic acid molecule comprising: i) a nucleotide sequence having at least about 96% sequence identity to SEQ ID NO: 1 or 5 or the complement thereof; or ii) a nucleotide sequence having at least, greater than or about 78% sequence identity to SEQ ID NO: 1, 5, 8 or 9 and encoding a polypeptide having cannabichromenic acid synthase activity; operably linked to a heterologous nucleic acid sequence suitable for expression in a cell or organism.

Also provided is a vector construct comprising: i) a nucleotide sequence having at least about 96% sequence identity to SEQ ID NO: 1 or 5 or the complement thereof;

or ii) a nucleotide sequence having at least, greater than or about 78% sequence identity to SEQ ID NO: 1, 5, 8 or 9 and encoding a polypeptide having cannabichromenic acid synthase activity; operably linked to a heterologous nucleic acid sequence suitable for expression in a cell or organism.

Another aspect includes a cell or organism comprising a nucleic acid comprising: a nucleotide sequence having at least about 96% sequence identity to SEQ ID NO: 1 or 5 or a nucleotide sequence having at least, greater than or about 78% sequence identity to SEQ ID NO: 1, 5, 8 or 9 and encoding a polypeptide having cannabichromenic acid synthase activity, and/or expressing a recombinant polypeptide comprising an amino acid sequence having at least about 95% sequence identity to SEQ ID NO: 2 or 6.

A further aspect includes a composition comprising an isolated nucleic acid, isolated polypeptide, vector construct, cell or antibody or fragment thereof described herein.

In a further aspect, there is provided a method of altering levels of cannabinoid compounds in an organism, cell or tissue, said method comprising expressing or over-expressing a nucleic acid molecule or polypeptide of the present disclosure in the organism, cell or tissue.

In another aspect, there is provided a method of altering levels of cannabinoid compounds in an organism, cell or tissue, said method comprising introducing a nucleic acid molecule or vector construct of the present disclosure or a fragment thereof, to silence and/or decrease expression of CBCAS in the organism, cell or tissue.

Cannabichromenic acid synthase, and the nucleotide sequence encoding this enzyme, have now been identified and characterized. The nucleotide sequence may be used to create, through selection or genetic engineering, cannabis plants that overproduce or under-produce cannabinoid compounds or mixtures thereof. Primers and probes comprising a fragment of the nucleotide sequence (e.g. at least 15 nucleotides in length) of SEQ ID NO: 1 and 5 may be used to identify mutants or variants in cannabichromenic acid synthase. This cannabichromenic acid synthase nucleotide sequence may also be expressed, alone or in combination with nucleic acid molecules encoding other enzymes in cannabinoid synthesis pathways, to engineer cannabinoid biosynthesis in other plants or in microorganisms (e.g. yeast, bacteria, fungi) or other prokaryotic or eukaryotic organisms. In addition, knocking out expression of this gene in cannabis could be used to block cannabinoid biosynthesis and thereby reduce production of cannabinoids.

Further features will be described or will become apparent in the course of the following detailed description.

BRIEF DESCRIPTION OF THE DRAWINGS

In order that the invention may be more clearly understood, embodiments thereof will now be described in detail by way of example, with reference to the accompanying drawings, in which.

DETAILED DESCRIPTION

Figure 1:
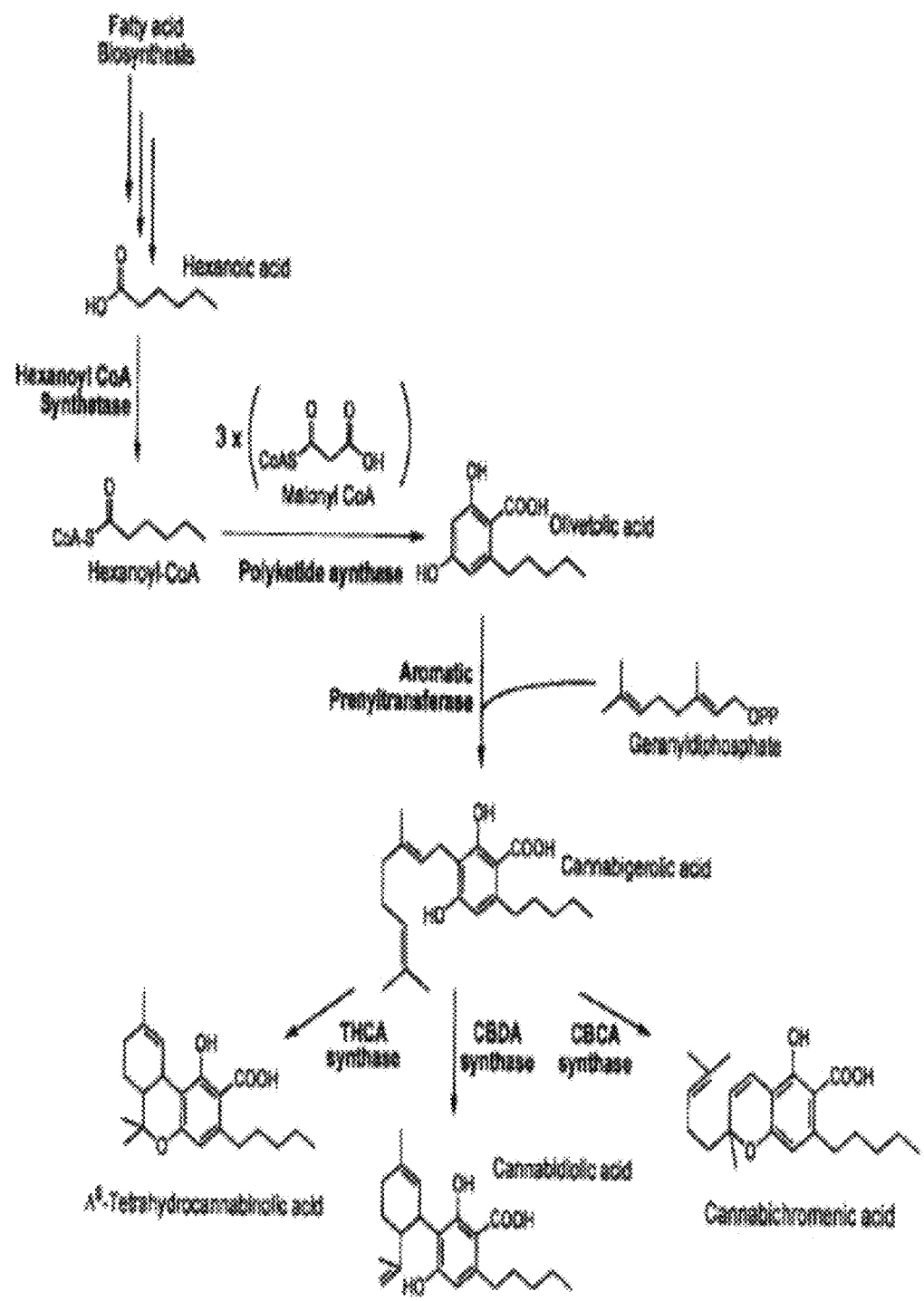
FIG. 1 depicts a proposed pathway leading to the main cannabinoid types in *Cannabis sativa*. Abbreviations: THCA synthase is $\Delta^9$-tetrahydrocannabinolic acid synthase, CBDA synthase is cannabidiolic acid synthase, and CBCA synthase is cannabichromenic acid synthase.

Described herein is a polynucleotide from *Cannabis sativa* which encodes CBCA synthase (CBCAS) and the encoded polypeptide. Methods of using said CBCAS, including through plant breeding, mutagenesis or genetic engineering, as well as methods for making recombinant cells, and recombinant organisms such as recombinant plants such as cannabis plants with enhanced CBCA content as well as cell free systems, are described. Furthermore, methods of inactivating or silencing CBCAS for example in a cannabis cell and/or plant are described, optionally to block and/or reduce CBCA biosynthesis and CBCA content of a cannabis cell or plant. Some embodiments describe use of said CBCA in combination with nucleic acids encoding other enzymes in the cannabinoid pathway.

As described herein, the cannabis genome sequence (van Bakel et al., 2011) was analyzed for genes with high similarity to THCA synthase using BLAST analysis, leading to the identification of a gene with 96% nucleotide similarity to THCA synthase. Based on the subsequent biochemical characterization, the identified gene was named *Cannabis sativa* cannabichromenic acid synthase (CBCAS).

The sequence of the CBCAS cDNA is provided in SEQ ID NO:1. SEQ ID NO: 1 includes a predicted signal sequence that is coded by nucleotides 1 to 84.

The corresponding amino acid sequence of the open reading frame of CBCAS is provided in SEQ ID NO:2. SEQ ID NO: 2 includes the predicted signal sequence which is found at amino acids 1-28. SEQ ID NO: 6 does not include the predicted signal sequence.

An embodiment provides an isolated nucleic acid that encodes the polypeptide encoded by SEQ ID NO: 2 or 6 or a fragment thereof.

In an embodiment, the isolated or purified nucleic acid is deleted of all or part of the nucleotides that encode the signal sequence, for example nucleotides 4-84 of SEQ ID NO:1, as shown in SEQ ID NO: 5.

The 5' codon ATG (and or additional codons optionally 1-50 additional codons, optionally 27 additional codonscan be replaced with another nucleic acid sequence, for example to introduce a sequence encoding a 5' heterologous moiety such as a tag or signal sequence for example alpha mating factor signal sequence.

In an embodiment, the isolated or purified polypeptide is deleted of all or part of the signal sequence, for example amino acids 1-28 or all or part of 2-28 of SEQ ID NO: 2, as shown in SEQ ID NO: 6.

The 5' methionine and/or additional amino acids at the 5' end (for example up to 50 additional amino acids) can be replaced with another amino acid sequence such as a 5' heterologous moiety such as a tag or signal sequence for example alpha mating factor signal sequence.

Other signal sequences can include for example α-amylase signal sequence from *Aspergillus niger*, Glucoamylase signal sequence from *Aspergillus awamori*, Serum albumin signal sequence from Homo sapiens, Inulinase signal sequence from *Kluyveromcyes maxianus*, Invertase signal sequence from *Saccharomyces cerevisiae*, Killer protein signal sequence from *Saccharomyces cerevisiae* or Lysozyme signal sequence from *Gallus gallus*.

The signal sequence of CBCAS can also be mutated by adding arginine residues or replacing amino acids with arginine residues.

SEQ ID NOs: 8 and 9 provide codon optimized nucleic acid sequences, optimized for *E. coli* and yeast respectively. Accordingly, in an embodiment, the sequence is a codon optimized sequence. The codon optimized sequences share about 78% and 79% sequence identity with SEQ ID NO: 1 and encode SEQ ID NO:2. In an embodiment, the optimized sequences are deleted of all or part of the corresponding predicted signal sequence nucleotides. In an embodiment, the signal sequence is replaced with another signal sequence or deleted and replaced with a methionine start codon.

Some embodiments relate to an isolated or purified nucleic acid molecule having at least or about 78%, at least or about 80%, at least or about 81%, at least or about 82%, at least or about 83%, at least or about 84%, at least or about 85%, at least or about 86%, at least or about 87%, at least or about 88%, at least or about 89%, at least or about 90%, at least or about 91%, at least or about 92%, at least or about 93%, at least or about 94%, at least or about 95%, at least or about 96%, at least or about 97%, at least or about 98% or at least or about 99% sequence identity to SEQ ID NO: 1, 5, 8 and/or 9. In certain embodiments, the isolated or purified nucleic acid molecule is a codon degenerate sequence of SEQ ID NO: 1, 5, 8 or 9. In an embodiment the nucleic acid molecule has cannabichromenic acid synthase activity.

Fragments of the above sequences including fragments of SEQ ID NO: 1, 5, 8 and 9 and sequences with at least or about 78% or more sequence identity thereto are also contemplated. In some embodiments, the nucleic acid molecule comprises at least and/or up to or about 15, at least and/or up to or about 20 at least and/or up to or about 25, at least and/or up to or about 30, at least and/or up to or about 40 at least and/or up to or about 50, at least and/or up to or about 60, at least and/or up to or about 70, at least and/or up to or about 80, at least and/or up to or about 90, at least and/or up to 100, at least or up to or about 200, at least or up to or about 300, at least or up or about 400, at least or up to or about 500, at least or up to or about 600, at least or up to or about 700, at least or up to or about 800, at least or up to or about 900, at least or up to or about 1000, at least or up to or about 1100, at least or up to or about 1200, at least or up to or about 1300, at least or up to or about 1400 or at least or up to or about 1500 contiguous nucleotides of SEQ ID NO:1, 5, 8 or 9 or a sequence with at least or about 78% or more, for example about 96% sequence identity thereto. For example, the nucleic acid molecule can be from 15 contiguous nucleotides up to 1500 contiguous nucleotides or any range or number of nucleotides there between.

Further included are nucleic acid molecules that hybridize to the above disclosed sequences. Hybridization conditions may be stringent in that hybridization will occur if there is at least about a 96% or about a 97% sequence identity with the nucleic acid molecule in SEQ ID NO: 1 or 5. The stringent conditions may include those used for known Southern hybridizations such as, for example, incubation overnight at 42° C. in a solution having 50% formamide, 5×SSC (150 mM NaCl, 15 mM trisodium citrate), 50 mM sodium phosphate (pH 7.6), 5×Denhardt's solution, 10% dextran sulfate, and 20 mg/mL denatured, sheared salmon sperm DNA, following by washing the hybridization support in 0.1×SSC at about 65° C. Other known hybridization conditions are well known and are described in Sambrook et al., Molecular Cloning: A Laboratory Manual, Third Edition, Cold Spring Harbor, N.Y. (2001).

As will be appreciated by the skilled practitioner, changes in nucleic acid sequence do not necessarily alter the amino acid sequence of the encoded polypeptide. It will be appreciated by persons skilled in the art that changes in the identities of nucleotides in a specific nucleic acid sequence that change the amino acid sequence of the encoded polypeptide may result in reduced or enhanced effectiveness of the genes and that, in some applications (e.g., anti-sense, co suppression, or RNAi), partial sequences can be used. The ways in which the nucleotide sequence can be varied or shortened are well known to persons skilled in the art, as are ways of testing the effectiveness of the altered sequences. In certain embodiments, effectiveness may easily be tested by, for example, conventional gas chromatography. All such variations of the nucleic acid sequences are therefore included as part of the present disclosure.

As will be appreciated by one of skill in the art, the length of the nucleic acid molecule described above will depend on the intended use. For example, if the intended use is as a primer or probe, for example, for PCR amplification or for screening a library, the length of the nucleic acid molecule will be less than the full length sequence, such as a fragment of for example, about 15 to about 50 nucleotides, optionally at least about 15 nucleotides of SEQ ID NO:1, 5, 8 or 9 and/or its complement, optionally at least about 17 nucleotides of SEQ ID NO:1, 5, 8 or9 or its complement, optionally at least about 19 nucleotides of SEQ ID NO:1, 5, 8 or 9 or its complement, optionally at least about 21 nucleotides of SEQ ID NO:1, 5, 8 or 9 or its complement, optionally at least about 23 nucleotides of SEQ ID NO:1, 5, 8 or 9 or its complement, optionally at least about 25 nucleotides of SEQ ID NO:1, 5, 8 or 9 and/or its complement. In these embodiments, the primers or probes may be substantially identical to a highly conserved region of the nucleic acid sequence or may be substantially identical to either the 5' or 3' end of the DNA sequence. In some cases, these primers or probes may use universal bases in some positions so as to be 'substantially identical' but still provide flexibility in sequence recognition. It is of note that suitable primer and probe hybridization conditions are well known in the art.

In an embodiment, the nucleic acid molecule can be used as a primer and for example comprises the sequence of SEQ ID NO: 3 or 4.

In an embodiment, the nucleic acid is conjugated to and/or comprises a heterologous moiety, such as a unique tail, purification tag or detectable label.

The unique tail can be a specific nucleic acid sequence.

The nucleic acid can for example be end labelled (5' or 3') or the label can be incorporated randomly during synthesis.

Also provided in another embodiment is an isolated polynucleotide molecule comprising i) a nucleic acid molecule comprising at least about 15 nucleotides of SEQ ID NO: 1, 5, 8 or 9 (e.g. a fragment of SEQ ID NO:1, 5, 8 or 5=9), or a nucleic acid comprising 15 nucleotides and having at least about 96%, at least about 97%, at least about 98% or at least about 99% identity to SEQ ID NO:1, 5, 8 or 9 and ii) a heterologous moiety. In an embodiment, the nucleic acid molecule encodes a polypeptide comprising enzymatic activity.

In an embodiment, the heterologous moiety is a heterologous nucleic acid that encodes a heterologous polypeptide and the polynucleotide molecule encodes a fusion polypeptide.

Some embodiments relate to an isolated or purified polypeptide having at least at least about 96%, at least about 97%, at least about 98% or at least about 99% identity to the amino acid sequence as set forth in SEQ ID NO: 2 or 6.

Fragments of SEQ ID NO: 2 or 6 are also contemplated. In some embodiments, the polypeptide comprises at least and/or up to about 5, at least and/or up to or about 10, at least and/or up to or about 15, at least and/or up to or about 20 at least and/or up to or about 25, at least and/or up to or about 30, at least and/or up to or about 40 at least and/or up to or about 50, at least and/or up to or about 60, at least and/or up to or about 70, at least and/or up to or about 80, at least and/or up to or about 90, at least and/or up to or about 100; at least and/or up to or about 150, at least and/or up to or about 200, at least and/or up to or about 250, at least and/or up to or about 300, at least and/or up to or about 350, at least and/or up to or about 400, at least and/or up to or about 450, at least and/or up to or about 500 contiguous amino acids of SEQ ID NO:2 or 6.

In an embodiment, the fragment has at least about 96%, at least about 97%, at least about 98% or at least about 99% identity to the amino acid sequence as set forth in SEQ ID NO: 2 or 6.

In an embodiment, the isolated polypeptide is differentially glycosylated, non-glycosylated (e.g. devoid of N and/or O-linked glycosylation) and/or deglycosylated as compared to Cannabis produced CBCAS. For example, the isolated polypeptide can be deglycosylated using chemical or enzymatic methods, for example treatment with Endo Hf or a deglycosylation enzyme mix. The isolated polypeptide for example is differentially glycosylated due to expression in yeast or other expression system.

Other embodiments relate to an isolated or purified composite polypeptide comprising: i) a polypeptide comprising at least 5 amino acid residues of SEQ ID NO:2 or 6 and optionally having at least, greater than or about 96%, at least, greater than or about 97%, at least, greater than or about 98% or at least, greater than or about 99% identity to the amino acid sequence as set forth in SEQ ID NO:2 or 6 and ii) a heterologous moiety.

In an embodiment, the heterologous moiety is a heterologous polypeptide and the composite polypeptide is a fusion polypeptide. For example the heterologous polypeptide can be a signal sequence such as alpha mating factor signal sequence.

In an embodiment, the fusion polypeptide optionally comprises a peptide linker joining the polypeptide comprising all or part of SEQ ID NO:2 or 6 and the heterologous polypeptide.

In an embodiment, the heterologous moiety is a detectable label or tag.

The detectable label is preferably capable of producing, either directly or indirectly, a detectable signal. For example, the label may be radio-opaque or a radioisotope, such as $^{3}H$, $^{14}C$, $^{32}P$ (including for example radioactive phosphates), $^{35}S$, 123I, $^{125}I$, $^{131}I$; biotin, a fluorescent (fluorophore) or chemiluminescent (chromophore) compound, such as fluorescein isothiocyanate, rhodamine or luciferin; an enzyme, such as alkaline phosphatase, beta-galactosidase or horseradish peroxidase; an imaging agent; or a metal ion.

In another embodiment, the detectable signal is detectable indirectly, for example, using a secondary antibody.

In an embodiment, the tag is selected from a His tag, HA tag, FLAG tag, AviTag, Calmodulin tag, polyglutamate tag, Myc tag, S-tag, SBP tag, strep-tag, V5-tag, GFP-tag, GST-tag, and thioredoxin-tag.

Another aspect includes an antibody that specifically binds CBCAS, for example as shown in SEQ ID NO: 2 or 6.

In aspects, the antibody is a purified or isolated antibody. By "purified" or "isolated" is meant that a given antibody or fragment thereof, whether one that has been removed from nature (isolated from blood serum) or synthesized (produced by recombinant means), has been increased in purity, wherein "purity" is a relative term, not "absolute purity." In particular aspects, a purified antibody is 60% free, preferably at least about 75% free, and more preferably at least about 90% free from other components with which it is naturally associated or associated following synthesis.

A further aspect of the disclosure includes a composition comprising a nucleic acid, construct, polypeptide, antibody or fragment thereof and/or a cell described herein. The composition can comprise for example a suitable carrier, diluent or additive. For example, wherein the composition comprises an antibody or fragment thereof, the suitable carrier can be a protein such as BSA.

In an embodiment, the composition comprises an isolated nucleic acid, isolated construct, isolated polypeptide, isolated antibody or fragment thereof and/or an isolated cell described herein, optionally in combination with a suitable carrier, diluent or additive.

In an embodiment, the composition is a purified extract, for example of a recombinant cell or recombinant organism described herein, such as a recombinant plant extract comprising an increased level of one or more cannabinoids and/or CBCAS. In an embodiment, the recombinant plant extract comprises an increased level of one or more cannabinoids such as CBCA or CBC. Accordingly, an aspect includes a cannabinoid or a composition comprising a cannabinoid such as CBCA or CBC, produced according to a method or system described herein.

In an embodiment, the purified extract comprises the culture supernatant of a recombinant organism culture, for example a recombinant yeast cell culture wherein the CBCAS is secreted into the culture supernatant.

Also provided in another aspect is a fermentation system comprising a recombinant organism or cell, for example a recombinant yeast cell. The system can comprise CBGA and/or other substrates in combination with one or more enzymes or cells expressing one or more enzymes in the cannabinoid pathway.

Some embodiments relate to a construct or in vitro expression system containing an isolated or purified nucleic acid molecule having at least, greater than or about 78% or more optionally at least, greater than or about 96% sequence identity to SEQ ID NO: 1, 5, 8 or 9, optionally comprising a heterologous moiety. Accordingly, there is provided a method for preparing a construct or in vitro expression system including such a sequence, or a fragment thereof, for introduction of the sequence or partial sequence in a sense or anti-sense orientation, or a complement thereof, into a cell.

As used herein a "vector" refers to a nucleic acid used to transfer a nucleic acid (often recombinant) into a host cell.

As used herein 'construct' refers to an artificially created nucleic acid, comprising a delivery vector and a polynucleotide of interest, for example a vector comprising a polynucleotide described herein. The polynucleotide of interest can be cloned into a vector of interest to produce a construct.

In an embodiment, the vector is an expression vector. Possible expression vectors include but are not limited to cosmids, plasmids, or modified viruses (e.g. replication defective retroviruses, adenoviruses and adeno-associated viruses), so long as the vector is compatible with the host cell used. The expression vectors are "suitable for transformation of a host cell", which means that the expression vectors contain a nucleic acid molecule of the application and regulatory sequences selected on the basis of the host cells to be used for expression, which is operatively linked to the nucleic acid molecule. Operatively linked is intended to mean that the nucleic acid is linked to regulatory sequences in a manner which allows expression of the nucleic acid.

In some embodiments, the isolated and/or purified nucleic acid molecules, polynucleotides or vectors, constructs or in vitro expression systems comprising these isolated and/or purified nucleic acid molecules, may be used to create transgenic or recombinant organisms or recombinant cells (e.g. optionally cells of recombinant organisms) that produce polypeptides with cannabichromenic acid synthase activity and/or modulated levels of polypeptides with cannabichromenic acid synthase activity.

Therefore, one embodiment relates to a recombinant organism, host cell or germ tissue (e.g. seed) of the organism comprising a nucleic acid molecule having at least 15 contiguous nucleotides of SEQ ID NO:1 and 5 and optionally at least about 96% sequence identity to SEQ ID NO: 1 or 5 and/or a construct comprising said isolated and/or purified nucleic acid molecule.

In an embodiment, the recombinant organism, cell and/or germ tissue expresses a polypeptide having at least and/or up to about 150, about 175, about 200, about 225, or about 250 amino acids of the polypeptide sequence and optionally at least about 96% sequence identity to as set forth in SEQ ID NO:2 or 6.

The recombinant expression vectors may also contain nucleic acid sequences which encode a heterologous polypeptide (e.g. fusion moiety) producing a fusion polypeptide when a nucleic acid of interest encoding a polypeptide is introduced into the vector in frame. The heterologous polypeptide can provide for increased expression of the recombinant protein; increased solubility of the recombinant protein; and/or aid in the purification of the target recombinant protein by acting as a ligand in affinity purification. For example, a proteolytic cleavage site may be added between the target recombinant protein to allow separation of the recombinant protein from the fusion moiety subsequent to purification of the fusion polypeptide. Typical fusion expression vectors include pGEX (Amrad Corp., Melbourne, Australia), pMal (New England Biolabs, Beverly, Mass.) and pRIT5 (Pharmacia, Piscataway, N.J.) which fuse glutathione S-transferase (GST), maltose E binding protein, or protein A, respectively, to the recombinant protein.

Preferably, the recombinant organism is a recombinant plant, recombinant multicellular microorganism or recombinant insect. Plants are preferably of the genus *Cannabis*, for example *Cannabis sativa L., Cannabis indica Lam.* and *Cannabis ruderalis Janisch*, especially *Cannabis sativa*. Microorganisms are preferably bacteria (e.g. *Escherichia coli*) or yeast (e.g. *Saccharomyces cerevisiae, Pichia pastoris*). Microorganisms that are unicellular can be considered organisms or cells, including host cells. Insect is preferably *Spodoptera frugiperda*.

*Cannabis* plants containing the CBCAS nucleotide sequence may be created via known plant transformation methods for example *Agrobacterium*-mediated transformation, transformation via particle bombardment, pollen tube or protoplast transformation. In these methodological approaches, the gene of interest is incorporated into the genome of the target organism. For example, tissue culture and *Agrobaterium* mediated transformation of hemp is described in Feeney and Punja, 2003.

Recombinant expression vectors can be introduced into host cells to produce a transformed host cell. Prokaryotic and/or eukaryotic cells can be transformed with nucleic acid by, for example, electroporation or calcium chloride-mediated transformation. For example, nucleic acid can be introduced into mammalian cells via conventional techniques such as calcium phosphate or calcium chloride co-precipitation, DEAE-dextran mediated transfection, lipofectin, viral mediated methods, electroporation or microinjection. Suitable methods for transforming and transfecting cells can be found in Sambrook et al. (Molecular Cloning: A Laboratory Manual, 3rd Edition, Cold Spring Harbor Laboratory Press, 2001), and other laboratory textbooks.

Suitable host cells include a wide variety of eukaryotic cells and prokaryotic cells. For example, the nucleic acids and proteins of the disclosure may be expressed in plant cells, yeast cells or mammalian cells. Plant cells are preferably of the genus *Cannabis*, for example *Cannabis sativa L., Cannabis indica Lam.* and *Cannabis ruderalis Janisch*, especially *Cannabis sativa*. Microorganisms are preferably bacteria (e.g. *Escherichia coli*) or yeast (e.g. *Saccharomyces cerevisiae, Pichia pastoris*). Insect cells are preferably *Spodoptera frugiperda* cells.

Accordingly an embodiment includes a recombinant cell and in a preferred embodiment the recombinant cell is a recombinant plant cell. In another preferred embodiment, the recombinant cell is a recombinant yeast cell.

Other suitable host cells can be found in Goeddel, Gene Expression Technology: Methods in Enzymology 185, Academic Press, San Diego, Calif. (1991). In addition, the proteins of the disclosure may be expressed in prokaryotic cells, such as *Escherichia coli* (Zhang et al., Science 303 (5656): 371-3 (2004)). In addition, a Pseudomonas-based expression system such as Pseudomonas fluorescens can be used (US Patent Application Publication No. US 2005/0186666).

Accordingly, also provided herein is a recombinant cell comprising a nucleic acid molecule or polynucleotide of the disclosure. In an embodiment, the nucleic acid molecule results in an increased level of cannabichromenic acid synthase.

Recombinant organisms, cells and germ tissues described herein may have altered levels of cannabinoid compounds. With reference to FIG. 1, it will be appreciated by one skilled in the art that expression or over-expression of the nucleic acid molecule will result in expression or over-expression of the cannabichromenic acid synthase enzyme which may result in increased production of cannabinoid compounds such as cannabichromenic acid and cannabichromene. Silencing of cannabichromenic acid synthase in an organism, cell or tissue will result in under-expression of the cannabichromenic acid synthase which may result in accumulation of higher amounts of cannabigerolic acid, cannabigerol, Δ9-tetrahydrocannabinolic acid, Δ9-tetrahydrocannabinol, cannabidiolic acid and cannabidiol or variants of these compounds having methyl or propyl sidechains. Germ tissues can include seeds, embryos or parts thereof comprising the isolated nucleic acid and/or polypeptide.

Expression or over-expression of the nucleic acid molecule may be done in combination with expression or over-expression of one or more other nucleic acids that encode one or more other enzymes in a cannabinoid biosynthetic pathway. Some examples of other nucleic acids include: nucleic acids that encode an hexanoyl-CoA synthetase, tetraketide synthase, olivetolic acid cyclase, a THCA synthase, a CBDA synthase and/or an aromatic prenyltransferase (e.g. CsPT1).

Expression or over-expression of the cannabichromenic acid synthase enzyme of the present disclosure compared to a control which has normal levels of the enzyme for the same variety grown under similar or identical conditions will result in increased levels of cannabinoid compounds, for example, about 1-about 20%, about 2-about 20%, about 5-about 20%, about 10-about 20%, about 15-about 20%, about 1-about 15%, about 1-about 10%, about 2-about 15%, about 2-about 10%, about 5-about 15%, or about 10-about 15% (w/w).

Accordingly, another aspect includes a method of altering levels of cannabinoid compounds in an organism, cell or tissue, said method comprising using a nucleic acid molecule of the present disclosure or a fragment thereof, to silence and/or decrease expression of CBCAS in the organism, cell or tissue.

In an embodiment, CBCA and CBC can be altered and/or produced in a cell or organism that produces CBGA, or in cells and organisms producing CBCA and/or CBC, the production of CBCA and/or CBC may be increased by making recombinant cells expressing CBCAS.

Another aspect includes an in vitro method of producing CBCA comprising: contacting CBGA with CBCAS in a solution or an immobilized state under suitable conditions and for a suitable time to produce CBCA and/or CBC; and isolating and/or purifying the CBCA and/or CBC.

The contacting can for example be achieved by mixing the CBGA with recombinant CBCAS in a solution and/or in an immobilized state under conditions and for a length of time suitable to convert at least about 10%, at least about 20%, at least about 30%, at least about 40%, at least about 50%, at least about 60%, at least about 70%, at least about 80%, at least about 90%, or at least about 100% of the CBGA to CBCA.

The solution optionally comprises MES, citrate or phosphate buffer, with the pH of the solution optionally between about pH 4 and about pH 6.5, or optionally about pH 4, about pH 4.5, about pH 5 about pH 5.5, about pH 6, or about pH 6.5.

The in vitro assay is optionally carried out at a temperature between 35° C. and 50° C., or about any temperature there between (e.g. any 0.1° C. increment between about 35° C. and about 50° C.) optionally at about 35° C., about 40° C., about 45° C. or about 50° C.

The CBCAS can be immobilized, for example, to a bead or column resin and used for example in in vitro systems.

Cannabichromene (CBC), the decarboxylated product of CBCA, does not contribute significantly to the psychoactivity of marijuana but shows THC-like activity in a mouse tetrad model at high concentrations (DeLong et al., 2011). In addition, CBC has been reported to cause numerous pharmacological and biological effects including analgesia (Davis and Hatoum, 1983) and antinocieptin (Maione et al., 2011) and possesses anti-inflammatory (DeLong et al. 2011; Wirth et al., 1980; Izzo et al. 2012), antifungal (Elsohly and Turner, 1982), antibiotic (Elsohly and Turner, 1982) and antitumour (Ligresti et al. 2006) activities.

A further aspect includes a method of producing CBCA and/or CBC and/or increasing production of CBCA and/or CBC the method comprising:
i) introducing into a cell or organism producing CBGA, a vector comprising a nucleic acid comprising SEQ ID NO:1, 5, 8 or 9, or a fragment thereof retaining CBCAS activity, optionally having at least or about 78% or more optionally 96% sequence identity to SEQ ID NO: 1, 5, 8 or 9 to produce a recombinant cell or recombinant organism;
ii) culturing the recombinant cell and/or growing the recombinant organism under conditions that permit expression of the nucleic acid; and optionally
iii) isolating and/or purifying CBCA and/or CBC.

The recombinant cell can be transiently expressing, inducibly expressing and/or stabley expressing.

In an embodiment, the method comprises heating and/or storing the CBCA to produce CBC. Storing and/or heating CBCA increases decarboxylation to CBC. For example, thermal decarboxylation of THCA and CBDA have been shown to occur at temperatures >94° C. (Veress et al 1990). Accordingly in an embodiment the CBCA is heated to at least about 94° C., optionally for at least or about 20 min, at least or about 30 min, at least or about 40 min, at least or about 50 min or at least or about 60 minutes or longer. In another embodiment CBCA is heated to at least about 105° C., optionally for at least or about 10 min, at least or about 20 min, at least or about 30 min, at least or about 40 min, at least or about 50 min, or at least or about 60 min or longer. In another embodiment CBCA is heated to at least about 120° C., optionally for at least or about 10 min, at least or about 15 min, at least or about 20 min, at least or about 25 min, at least or about 30 min, at least or about 35 min, at least or about 40 min, at least or about 45 min, at least or about 50 min. In yet another embodiment CBCA is heated to at least about 140° C., optionally for at least or about 5 min, at least or about 10 min, at least or about 15 min, at least or about 20 min, or at least or about 25 min. In another embodiment the temperature is any 0.1° C. increment between about 94° C. and about 150° C. and the time of heating is any 1 min increment between about 3 and about 90 min.

In an embodiment, neutral and acidic cannabinoids are isolated and/or purified. In an embodiment, neutral cannabinoids are isolated and/or purified. In an embodiment, acidic cannabinoids are isolated and/or purified.

Another aspect includes a method of producing CBC and/or increasing CBC production, the method comprising:
i) introducing into a cell or organism producing CBGA a vector comprising a nucleic acid comprising all or a fragment of SEQ ID NO:1, 5, 8 or 9, the fragment having CBCAS activity, optionally having at least about 96% identity to SEQ ID NO: 1, 5, 8 or 9 to produce a recombinant cell or recombinant organism;
ii) culturing the recombinant cell and/or growing the recombinant organism under conditions that permit expression of the nucleic acid;
iii) isolating CBCA; and
iv) heating and/or storing the CBCA to produce CBC.

In an embodiment, the cell is a plant cell. In an embodiment the plant cell is cannabis cell. In another embodiment, the cell is a non-cannabis cell.

In cannabis plants the enhanced production of cannabinoids or the reduction/removal of cannabinoids could be achieved through breeding and selection as well as genetic engineering with the use of genes encoding the enzymes of cannabinoid biosynthetic pathways, e.g. the CBCA synthase gene in this disclosure. In addition, the biosynthetic pathway leading to cannabinoids may be transferred to bacteria, yeast, fungi or other heterologous organisms, or by in vitro biocatalysts, to produce cannabinoids without the need for the cannabis plant.

In an embodiment, the organism is a plant. In an embodiment, the plant is cannabis plant.

Nucleic acid isolation and cloning is well established. Similarly, an isolated gene may be inserted into a vector and transformed into a cell by conventional techniques. Nucleic acid molecules may be transformed into a cell and/or an organism. As known in the art, there are a number of ways by which genes, vectors and constructs can be introduced into cells and/or organisms, and a combination of transformation and tissue culture techniques have been successfully integrated into effective strategies for creating recombinant cells and/or organisms. These methods, which can be used herein have been described elsewhere (Potrykus, 1991; Vasil, 1994; Walden and Wingender, 1995; Songstad et al., 1995), and are well known to persons skilled in the art. Suitable vectors are well known to those skilled in the art and are described in general technical references such as Pouwels et al., (1986). Particularly suitable vectors include the Ti plasmid vectors. For example, one skilled in the art will certainly be aware that, in addition to *Agrobacterium* mediated transformation of *Arabidopsis* by vacuum infiltration (Bechtold, et al. 1993) or wound inoculation (Katavic et al., 1994), it is equally possible to transform other plant species, using *Agrobacterium* Ti-plasmid mediated transformation (e.g., hypocotyl (DeBlock et al., 1989) or cotyledonary petiole (Moloney et al., 1989) wound infection), particle bombardment/biolistic methods (Sanford et al., 1987; Nehra. et al., 1994; Becker et al., 1994) or polyethylene glycol-assisted, protoplast transformation (Rhodes et al., 1988; Shimamoto et al., 1989) methods.

In an embodiment, the recombinant cell or organism is a transgenic cell or transgenic organism. In an embodiment, the recombinant cell or organism comprises an episome comprising the isolated polynucleotide.

The recombinant expression vector in addition to containing a nucleic acid molecule or polynucleotide disclosed herein, may contain regulatory sequences for the transcription and translation of the inserted nucleic acid molecule.

Suitable regulatory sequences may be derived from a variety of sources, including bacterial, fungal, viral, mammalian, or insect genes (For example, see the regulatory sequences described in Goeddel, Gene Expression Technology: Methods in Enzymology 185, Academic Press, San Diego, Calif. (1990)). Selection of appropriate regulatory sequences is dependent on the host cell chosen as discussed below, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector.

As will also be apparent to persons skilled in the art, and as described elsewhere (Meyer, 1995; Datla et al., 1997), it is possible to utilize promoters to direct any intended up- or down-regulation of transgene expression using constitutive promoters (e.g., those based on CaMV35S), or by using promoters which can target gene expression to particular cells, tissues (e.g., napin promoter for expression of transgenes in developing seed cotyledons), organs (e.g., roots, leaves), to a particular developmental stage, or in response to a particular external stimulus (e.g., heat shock).

Promoters for use herein may be inducible, constitutive, or tissue-specific or have various combinations of such characteristics. Useful promoters include, but are not limited to constitutive promoters such as carnation etched ring virus (CERV), cauliflower mosaic virus (CaMV) 35S promoter, or more particularly the double enhanced cauliflower mosaic virus promoter, comprising two CaMV 35S promoters in tandem (referred to as a "Double 35S" promoter). In an embodiment, the promoter is a promoter active in monocots, for example APX, SCP1, PGD1, R1G1B, or EIF5 promoter. It may be desirable to use a tissue-specific or developmentally regulated promoter instead of a constitutive promoter in certain circumstances. A tissue-specific promoter allows for over-expression in certain tissues without affecting expression in other tissues.

The promoter and termination regulatory regions will be functional in the host cell and may be heterologous (that is, not naturally occurring) or homologous (derived from the plant host species) to the cell and the gene. Suitable promoters which may be used are described above.

The termination regulatory region may be derived from the 3' region of the gene from which the promoter was obtained or from another gene. Suitable termination regions which may be used are well known in the art and include *Agrobacterium tumefaciens* nopaline synthase terminator (Tnos), *A. tumefaciens* mannopine synthase terminator (Tmas) and the CaMV 35S terminator (T35S). Particularly preferred termination regions for use herein include the pea ribulose bisphosphate carboxylase small subunit termination region (TrbcS) or the Tnos termination region. Such gene constructs may suitably be screened for activity by transformation into a host plant via *Agrobacterium* and screening for altered cannabinoid levels.

The recombinant expression constructs of the disclosure may also contain a selectable marker gene which facilitates the selection of host cells transformed or transfected with a recombinant molecule of the application. Examples of selectable marker genes are genes encoding a protein such as G418 and hygromycin which confer resistance to certain drugs, β-galactosidase, chloramphenicol acetyltransferase, firefly luciferase, or an immunoglobulin or portion thereof such as the Fc portion of an immunoglobulin, optionally IgG. Transcription of the selectable marker gene is monitored by changes in the concentration of the selectable marker protein such as β-galactosidase, chloramphenicol acetyltransferase, or firefly luciferase. If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of recombinant expression constructs of the application and in particular to determine the effect of a mutation on expression and phenotype. It will be appreciated that selectable markers can be introduced on a separate vector from the nucleic acid of interest.

The nucleic acid molecule or fragments thereof may be used to block cannabinoid biosynthesis in organisms that naturally produce cannabinoid compounds. Silencing using a nucleic acid molecule disclosed herein may be accomplished in a number of ways generally known in the art, for example, RNA interference (RNAi) techniques, artificial microRNA techniques, virus-induced gene silencing (VIGS) techniques, antisense techniques, sense co-suppression techniques and targeted mutagenesis techniques.

RNAi techniques involve stable transformation using RNA interference (RNAi) plasmid constructs (Helliwell and Waterhouse, 2005). Such plasmids are composed of a fragment of the target gene to be silenced in an inverted repeat structure. The inverted repeats are separated by a spacer, often an intron. The RNAi construct driven by a suitable promoter, for example, the Cauliflower mosaic virus (CaMV) 35S promoter, is integrated into the plant genome and subsequent transcription of the transgene leads to an RNA molecule that folds back on itself to form a double-stranded hairpin RNA. This double-stranded RNA structure is recognized by the plant and cut into small RNAs (about 21 nucleotides long) called small interfering RNAs (siRNAs). siRNAs associate with a protein complex (RISC) which goes on to direct degradation of the mRNA for the target gene.

Artificial microRNA (amiRNA) techniques exploit the microRNA (miRNA) pathway that functions to silence endogenous genes in plants and other eukaryotes (Schwab et al, 2006; Alvarez et al, 2006). In this method, about 21 nucleotide long fragments of the gene to be silenced are introduced into a pre-miRNA gene to form a pre-amiRNA construct. The pre-miRNA construct is transferred into the organism genome using transformation methods apparent to one skilled in the art. After transcription of the pre-amiRNA, processing yields amiRNAs that target genes which share nucleotide identity with the 21 nucleotide amiRNA sequence.

In RNAi silencing techniques, two factors can influence the choice of length of the fragment. The shorter the fragment the less frequently effective silencing will be achieved, but very long hairpins increase the chance of recombination in bacterial host strains. The effectiveness of silencing also appears to be gene dependent and could reflect accessibility of target mRNA or the relative abundances of the target mRNA and the hpRNA in cells in which the gene is active. A fragment length of between about 100 and about 800 bp, preferably between about 300 and about 600 bp, is generally suitable to maximize the efficiency of silencing obtained. The other consideration is the part of the gene to be targeted. 5' UTR, coding region, and 3' UTR fragments can be used with equally good results. As the mechanism of silencing depends on sequence homology there is potential for cross-silencing of related mRNA sequences. Where this is not desirable a region with low sequence similarity to other sequences, such as a 5' or 3' UTR, should be chosen. The rule for avoiding cross-homology silencing appears to be to use sequences that do not have blocks of sequence identity of over about 20 bases between the construct and the non-target gene sequences. Many of these same principles apply to selection of target regions for designing amiRNAs.

Virus-induced gene silencing (VIGS) techniques are a variation of RNAi techniques that exploits the endogenous antiviral defenses of plants. Infection of plants with recombinant VIGS viruses containing fragments of host DNA leads to post-transcriptional gene silencing for the target gene. In one embodiment, a tobacco rattle virus (TRV) based VIGS system can be used.

Antisense techniques involve introducing into a plant an antisense oligonucleotide that will bind to the messenger RNA (mRNA) produced by the gene of interest. The "antisense" oligonucleotide has a base sequence complementary to the gene's messenger RNA (mRNA), which is called the "sense" sequence. Activity of the sense segment of the mRNA is blocked by the anti-sense mRNA segment, thereby effectively inactivating gene expression. Application of antisense to gene silencing in plants is described in more detail by Stam et al., 2000.

Sense co-suppression techniques involve introducing a highly expressed sense transgene into a plant resulting in reduced expression of both the transgene and the endogenous gene (Depicker et al., 1997). The effect depends on sequence identity between transgene and endogenous gene.

Targeted mutagenesis techniques, for example TILLING (Targeting Induced Local Lesions IN Genomes) and "delete-a-gene" using fast-neutron bombardment, may be used to knockout gene function in an organism (Henikoff et al., 2004; Li et al., 2001). TILLING involves treating germplasm or individual cells with a mutagen to cause point mutations that are then discovered in genes of interest using a sensitive method for single-nucleotide mutation detection. Detection of desired mutations (e.g. mutations resulting in the inactivation of the gene product of interest) may be accomplished, for example, by sequencing methods. For example, oligonucleotide primers derived from the gene of interest may be prepared and PCR may be used to amplify regions of the gene of interest from organisms in the mutagenized population. Amplified mutant genes may be annealed to wild-type genes to find mismatches between the mutant genes and wild-type genes. Detected differences may be traced back to the organism which had the mutant gene thereby revealing which mutagenized organism will have the desired expression (e.g. silencing of the gene of interest). These organisms may then be selectively bred to produce a population having the desired expression. TILLING can provide an allelic series that includes missense and knockout mutations, which exhibit reduced expression of the targeted gene. TILLING is touted as a possible approach to gene knockout that does not involve introduction of transgenes, and therefore may be more acceptable to consumers. Fast-neutron bombardment induces mutations, i.e. deletions, in organism genomes that can also be detected using PCR in a manner similar to TILLING.

Terms:

To facilitate review of the various embodiments of the disclosure, the following explanations of specific terms are provided:

As used herein, the term "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

Antibody: The term "antibody" as used herein is intended to include monoclonal antibodies, polyclonal antibodies, and chimeric antibodies. The antibody may be from recombinant sources and/or produced in transgenic animals.

Antibody binding fragment: The term "antibody binding fragment" as used herein is intended to include Fab, Fab', F(ab')2, scFv, dsFv, ds-scFv, dimers, minibodies, diabodies, and multimers thereof and bispecific antibody fragments. Antibodies can be fragmented using conventional techniques. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments. Fab, Fab' and F(ab')2, scFv, dsFv, ds-scFv, dimers, minibodies, diabodies, bispecific antibody fragments and other fragments can also be synthesized by recombinant techniques.

Antibodies may be monospecific, bispecific, trispecific or of greater multispecificity. Multispecific antibodies may immunospecifically bind to different epitopes of a cannabichromenic acid synthase and/or or a solid support material.

Antibodies may be from any animal origin including birds and mammals (e.g., human, murine, donkey, sheep, rabbit, goat, guinea pig, camel, horse, or chicken).

Antibodies may be prepared using methods known to those skilled in the art. Isolated native or recombinant polypeptides may be utilized to prepare antibodies. See, for example, Kohler et al. (1975) Nature 256:495-497; Kozbor et al. (1985) J. Immunol. Methods, 81:31-42; Cote et al. (1983) Proc Natl Acad Sci., 80:2026-2030; and Cole et al. (1984) Mol Cell Biol., 62:109-120, for the preparation of monoclonal antibodies; Huse et al. (1989) Science, 246: 1275-1281, for the preparation of monoclonal Fab fragments; and, Pound (1998) Immunochemical Protocols, Humana Press, Totowa, N.J., for the preparation of phagemid or B-lymphocyte immunoglobulin libraries to identify antibodies.

Codon degeneracy: It will be appreciated that this disclosure embraces the degeneracy of codon usage as would be understood by one of ordinary skill in the art and as illustrated in Table 1. Codon optimized sequences are provided in Example 8.

TABLE 1

Codon Degeneracies

| Amino Acid | Codons |
| --- | --- |
| Ala/A | GCT, GCC, GCA, GCG |
| Arg/R | CGT, CGC, CGA, CGG, AGA, AGG |
| Asn/N | AAT, AAC |
| Asp/D | GAT, GAC |
| Cys/C | TGT, TGC |
| Gln/Q | CAA, CAG |
| Glu/E | GAA, GAG |
| Gly/G | GGT, GGC, GGA, GGG |
| His/H | CAT, CAC |
| Ile/I | ATT, ATC, ATA |
| Leu/L | TTA, TTG, CTT, CTC, CTA, CTG |
| Lys/K | AAA, AAG |
| Met/M | ATG |
| Phe/F | TTT, TTC |
| Pro/P | CCT, CCC, CCA, CCG |
| Ser/S | TCT, TCC, TCA, TCG, AGT, AGC |
| Thr/T | ACT, ACC, ACA, ACG |
| Trp/W | TGG |
| Tyr/Y | TAT, TAC |
| Val/V | GTT, GTC, GTA, GTG |
| START | ATG |
| STOP | TAG, TGA, TAA |

Conservative substitutions: Furthermore, it will be understood by one skilled in the art that conservative substitutions may be made in the amino acid sequence of a polypeptide without disrupting the structure or function of the polypeptide. Conservative amino acid substitutions are accomplished by the skilled artisan by substituting amino acids with similar hydrophobicity, polarity, and R-chain length for one another. Additionally, by comparing aligned sequences of homologous proteins from different species, conservative amino acid substitutions may be identified by locating amino acid residues that have been mutated between species without altering the basic functions of the encoded proteins. Table 2 provides an exemplary list of conservative substitutions.

TABLE 2

Conservative Substitutions

| Type of Amino Acid | Substitutable Amino Acids |
| --- | --- |
| Hydrophilic | Ala, Pro, Gly, Glu, Asp, Gln, Asn, Ser, Thr |
| Sulphydryl | Cys |
| Aliphatic | Val, Ile, Leu, Met |
| Basic | Lys, Arg, His |
| Aromatic | Phe, Tyr, Trp |

Complementary nucleotide sequence: "Complementary nucleotide sequence" of a sequence is understood as meaning any nucleic acid molecule whose nucleotides are complementary to those of sequence of the disclosure, and whose orientation is reversed (antiparallel sequence).

Degree or percentage of sequence homology: The term "degree or percentage of sequence homology" refers to degree or percentage of sequence identity between two sequences after optimal alignment. Percentage of sequence identity (or degree of identity) is determined by comparing two optimally aligned sequences over a comparison window, where the portion of the peptide or polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical amino-acid residue or nucleic acid base occurs in both sequences to yield the number of matched positions, dividing the number of matched positions by the total number of positions in the window of comparison and multiplying the result by 100 to yield the percentage of sequence identity.

Fusion molecule: The term "a fusion molecule" refers to the linking of a peptide sequence derived from the extracellular domain or domains of the polypeptide having cannabichromenic acid synthase activity (SEQ ID NO:2 or 6) to a fusion partner and can be a direct or indirect linkage via a covalent or non-covalent linkage. The fusion partner may be linked to either the N-terminus or the C-terminus of the peptide sequence derived from cannabichromenic acid synthase (SEQ ID NO:2 or 6).

Homologous isolated and/or purified sequence: "Homologous isolated and/or purified sequence" is understood to mean an isolated and/or purified sequence having a percentage identity with the bases of a nucleotide sequence, or the amino acids of a polypeptide sequence, of at least about 95%, about 96%, about 97%, about 98%, about 99%, about 99.5%, about 99.6%, or about 99.7%. This percentage is purely statistical, and it is possible to distribute the differences between the two nucleotide sequences at random and over the whole of their length. Sequence identity can be determined, for example, by computer programs designed to perform single and multiple sequence alignments. It will be appreciated that this disclosure embraces the degeneracy of codon usage as would be understood by one of ordinary skill in the art. Furthermore, it will be understood by one skilled in the art that conservative substitutions may be made in the amino acid sequence of a polypeptide without disrupting the structure or function of the polypeptide. Conservative substitutions are accomplished by the skilled artisan by substituting amino acids with similar hydrophobicity, polarity, and R-chain length for one another. Additionally, by comparing aligned sequences of homologous proteins from different species, conservative substitutions may be identified by locating amino acid residues that have been mutated between species without altering the basic functions of the encoded proteins.

Increasing, decreasing, modulating, altering or the like: As will be appreciated by one of skill in the art, such terms refer to comparison to a similar variety grown under similar conditions but without the modification resulting in the increase, decrease, modulation or alteration. In some cases, this may be an untransformed control, a mock transformed control, or a vector-transformed control.

Isolated: As will be appreciated by one of skill in the art, "isolated" refers to for example polypeptides or nucleic acids that have been "isolated" from their native environment, including but not limited to virus, proteins, glycoproteins, peptide derivatives or fragments or polynucleotides. For example the term "isolated nucleic acid molecule" as used herein refers to a nucleic acid substantially free of cellular material or culture medium when produced by recombinant DNA techniques, or chemical precursors, or other chemicals when chemically synthesized. An isolated nucleic acid is also substantially free of sequences, which naturally flank the nucleic acid (i.e. sequences located at the 5' and 3' ends of the nucleic acid) from which the nucleic acid is derived.

In vitro expression system: The term "in vitro expression system" as used herein is understood to refer to reagents and components (e.g. in a kit) and/or solutions comprising said reagents and components for recombinant protein expression, wherein the in vitro expression system is cell free and includes optionally translation competent extracts of whole cells and/or other translation machinery reagents or components optionally in a solution, said reagents and components optionally including RNA polymerase, one or more regulatory protein factors, one or more transcription factors, ribosomes, and tRNA, optionally supplemented with cofactors and nucleotides, and the specific gene template of interest. Chemical based expression systems are also included, optionally using unnaturally occurring amino acids.

In an embodiment, the in vitro expression system comprises a vector optionally with a 5' T7 promoter downstream of which the isolated polynucleotide is introduced.

Polynucleotide, or nucleic acid molecule: "Polynucleotide, or nucleic acid molecule" will be understood as meaning double-stranded or single-stranded in the monomeric and dimeric (so-called in tandem) forms and the transcription products thereof, as well as complementary nucleic acid sequences. Polynucleotide and nucleic acid molecules includes a sequence of nucleoside or nucleotide monomers consisting of naturally occurring bases, sugars and intersugar (backbone) linkages. The term also includes modified or substituted sequences comprising non-naturally occurring monomers or portions thereof. The nucleic acid sequences of the present disclosure may be deoxyribonucleic acid sequences (DNA) or ribonucleic acid sequences (RNA) and may include naturally occurring bases including adenine, guanine, cytosine, thymidine and uracil. The sequences may also contain modified bases. Examples of such modified bases include aza and deaza adenine, guanine, cytosine, thymidine and uracil; and xanthine and hypoxanthine. In an embodiment, the polynucleotide or nucleic acid molecule is a cDNA.

Protein or polypeptide: "Protein or polypeptide" will be understood as meaning a sequence of amino acid residues encoded by a nucleic acid molecule. Within the context of the present application, a polypeptide of the disclosure may in one embodiment include various structural forms of the primary protein. For example, a polypeptide of the disclosure may be in the form of acidic or basic salts or in neutral form. In addition, individual amino acid residues may be modified by oxidation or reduction. The proteins and polypeptides of the present disclosure may also include truncations, analogs and homologs of the proteins and polypeptides as described herein having substantially the same function as the proteins or polypeptides of the present disclosure, such as having cannabichromenic acid synthase activity.

Sequence identity: Two amino-acids or nucleotide sequences are said to be "identical" if the sequence of amino-acids or nucleotide residues in the two sequences is the same when aligned for maximum correspondence as described below. Sequence comparisons between two (or more) peptides or polynucleotides are typically performed by comparing sequences of two optimally aligned sequences over a segment or "comparison window" to identify and compare local regions of sequence similarity. Optimal alignment of sequences for comparison may be conducted by the local homology algorithm of Smith and Waterman, Ad. App. Math 2: 482 (1981), by the homology alignment algorithm of Needleman and Wunsch, J. Mol. Biol. 48: 443 (1970), by the search for similarity method of Pearson and Lipman, Proc. Natl. Acad. Sci. (U.S.A.) 85: 2444 (1988), by computerized implementation of these algorithms (GAP, BEST-FIT, FASTA, and TFASTA in the Wisconsin Genetics Software Package, Genetics Computer Group (GCG), 575 Science Dr., Madison, Wis.), or by visual inspection.

The definition of sequence identity given above is the definition that would be used by one of skill in the art. The definition by itself does not need the help of any algorithm, said algorithms being helpful only to achieve the optimal alignments of sequences, rather than the calculation of sequence identity.

From the definition given above, it follows that there is a well defined and only one value for the sequence identity between two compared sequences which value corresponds to the value obtained for the best or optimal alignment.

Fragment thereof: As used herein, the term "fragment thereof" interchangeably used with "part" refers to a nucleic acid or amino acid sequence comprising up to about 3, about 5, about 10, about 15, about 25, about 50, about 100, about 250 or about 500, contiguous residues of a nucleotide or amino acid sequence of interest, for example comprising up to about 3, about 5, about 10, about 15, about 25, about 50, about 100, about 200, about 250, about 300, about 400, about 500, about 600, about 700, about 800, about 900, about 1000, about 1100, about 1200, about 1300, about 1400, or about 1500 nucleotides of SEQ ID NO:1 or comprising up to about 3, about 5, about 10, about 15, about 25, about 50, about 100, about 200, about 250, about 300, about 400, or about 500 amino acids of SEQ ID NO: 2.

Stringent hybridization: Hybridization under conditions of stringency with a nucleotide sequence is understood as meaning a hybridization under conditions of temperature and ionic strength chosen in such a way that they allow the maintenance of the hybridization between two fragments of complementary nucleic acid molecules. Homologs of the CBCAS gene described herein obtained from other organisms, for example plants, may be obtained by screening appropriate libraries that include the homologs, wherein the screening is performed with the nucleotide sequence of the specific CBCAS gene disclosed herein, or portions or probes thereof, or identified by sequence homology search using sequence alignment search programs such as BLAST, FASTA.

The terms "transformed with", "transfected with", "transformation" and "transfection" are intended to encompass introduction of nucleic acid (e.g. a construct) into a cell by one of many possible techniques known in the art.

A single-stranded nucleic acid molecule is "complementary" to another single-stranded nucleic acid molecule when it can base-pair (hybridize) with all or a portion of the other nucleic acid molecule to form a double helix (double-stranded nucleic acid molecule), based on the ability of guanine (G) to base pair with cytosine (C) and adenine (A) to base pair with thymine (T) or uridine (U).

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Finally, terms of degree such as "substantially", "about" and "approximately" as used herein mean a reasonable amount of deviation of the modified term such that the end result is not significantly changed. These terms of degree should be construed as including a deviation of at least ±10% of the modified term if this deviation would not negate the meaning of the word it modifies In understanding the scope of the present disclosure, the term "consisting" and its derivatives, as used herein, are intended to be close ended terms that specify the presence of stated features, elements, components, groups, integers, and/or steps, and also exclude the presence of other unstated features, elements, components, groups, integers and/or steps.

The recitation of numerical ranges by endpoints herein includes all numbers and fractions subsumed within that range (e.g. about 1 to about 5 includes 1, 1.5, 2, 2.75, 3, 3.90, 4, and 5). It is also to be understood that all numbers and fractions thereof are presumed to be modified by the term "about." Further, it is to be understood that "a," "an," and "the" include plural referents unless the content clearly dictates otherwise.

Further, the definitions and embodiments described in particular sections are intended to be applicable to other embodiments herein described for which they are suitable as would be understood by a person skilled in the art. For example, in the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous. The above disclosure generally describes the present application. A more complete understanding can be obtained by reference to the following specific examples. These examples are described solely for the purpose of illustration and are not intended to limit the scope of the application. Changes in form and substitution of equivalents are contemplated as circumstances might suggest or render expedient. Although specific terms have been employed herein, such terms are intended in a descriptive sense and not for purposes of limitation.

All publicly available documents referenced herein, including but not limited to US patents, are specifically incorporated by reference.

The following non-limiting examples are illustrative of the present disclosure:

EXAMPLES

Example 1: Identification of CBCA Synthase in the Cannabis Genome

The cannabis genome sequence (van Bakel et al., 2011) was analyzed for genes with high similarity to THCA synthase using BLAST analysis. This led to the identification of a gene with 96% nucleotide similarity to THCA synthase. Based on subsequent biochemical characterization, the authors named this gene *Cannabis sativa* cannabichromenic acid synthase (CBCAS).

The cDNA sequence of *Cannabis sativa* cannabichromenic acid synthase (CBCAS)—1635 bp is provided in SEQ ID NO:1. Underlined sequence relates to the sequence deleted in SEQ ID NO:5. SEQ ID NO: 1 can comprise the full sequence or deleted of replicates of 3 in the underlined sequence and/or the first ATG to maintain coding frame.

```
ATGAATTGCTCAACATTCTCCTTTTGGTTTGTTTGCAAAATAATATTTTT
CTTTCTCTCATTCAATATCCAAATTTCAATAGCTAATCCTCAAGAAAACT
TCCTTAAATGCTTCTCGGAATATATTCCTAACAATCCAGCAAATCCAAAA
TTCATATACACTCAACACGACCAATTGTATATGTCTGTCCTGAATTCGAC
AATACAAAATCTTAGATTCACCTCTGATACAACCCCAAAACCACTCGTTA
TTGTCACTCCTTCAAATGTCTCCCATATCCAGGCCAGTATTCTCTGCTCC
AAGAAAGTTGGTTTGCAGATTCGAACTCGAAGCGGTGGCCATGATGCTGA
GGGTTTGTCCTACATATCTCAAGTCCCATTTGCTATAGTAGACTTGAGAA
ACATGCATACGGTCAAAGTAGATATTCATAGCCAAACTGCGTGGGTTGAA
GCCGGAGCTACCCTTGGAGAAGTTTATTATTGGATCAATGAGATGAATGA
GAATTTTAGTTTTCCTGGTGGGTATTGCCCTACTGTTGGCGTAGGTGGAC
ACTTTAGTGGAGGAGGCTATGGAGCATTGATGCGAAATTATGGCCTTGCG
GCTGATAATATCATTGATGCACACTTAGTCAATGTTGATGGAAAAGTTCT
AGATCGAAAATCCATGGGAGAAGATCTATTTTGGGCTATACGTGGTGGAG
GAGGAGAAAACTTTGGAATCATTGCAGCATGTAAAATCAAACTTGTTGTT
GTCCCATCAAAGGCTACTATATTCAGTGTTAAAAAGAACATGGAGATACA
TGGGCTTGTCAAGTTATTTAACAAATGGCAAAATATTGCTTACAAGTATG
ACAAAGATTTAATGCTCACGACTCACTTCAGAACTAGGAATATTACAGAT
AATCATGGAAGAATAAGACTACAGTACATGGTTACTTCTCTTCCATTTT
TCTTGGTGGAGTGGATAGTCTAGTTGACTTGATGAACAAGAGCTTTCCTG
AGTTGGGTATTAAAAAAACTGATTGCAAAGAATTGAGCTGGATTGATACA
ACCATCTTCTACAGTGGTGTTGTAAATTACAACACTGCTAATTTTAAAAA
GGAAATTTTGCTTGATAGATCAGCTGGGAAGAAGACGGCTTTCTCAATTA
AGTTAGACTATGTTAAGAAACTAATACCTGAAACTGCAATGGTCAAAATT
TTGGAAAAATTATATGAAGAAGAGGTAGGAGTTGGGATGTATGTGTTGTA
CCCTTACGGTGGTATAATGGATGAGATTTCAGAATCAGCAATTCCATTCC
CTCATCGAGCTGGAATAATGTATGAACTTTGGTACACTGCTACCTGGGAG
```

-continued
AAGCAAGAAGATAACGAAAAGCATATAAACTGGGTTCGAAGTGTTTATAA

TTTCACAACTCCTTATGTGTCCCAAAATCCAAGATTGGCGTATCTCAATT

ATAGGGACCTTGATTTAGGAAAAACTAATCCTGAGAGTCCTAATAATTAC

ACACAAGCACGTATTTGGGGTGAAAAGTATTTTGGTAAAAATTTTAACAG

GTTAGTTAAGGTGAAAACCAAAGCTGATCCCAATAATTTTTTTAGAAACG

AACAAAGTATCCCACCTCTTCCACCGCGTCATCAT

The corresponding amino acid sequence of the open reading form of Cannabis sativa cannabichromenic acid synthase (CBCAS)—545 aa is provided in SEQ ID NO:2 (and can include all or part of the first 28 amino acids).

MNCSTFSFWFVCKIIFFFLSFNIQISIANPQENFLKCFSEYIPNNPANPK

FIYTQHDQLYMSVLNSTIQNLRFTSDTTPKPLVIVTPSNVSHIQASILCS

KKVGLQIRTRSGGHDAEGLSYISQVPFAIVDLRNMHTVKVDIHSQTAWVE

AGATLGEVYYWINEMNENFSFPGGYCPTVGVGGHFSGGGYGALMRNYGLA

ADNIIDAHLVNVDGKVLDRKSMGEDLFWAIRGGGGENFGIIAACKIKLVV

VPSKATIFSVKKNMEIHGLVKLFNKWQNIAYKYDKDLMLTTHFRTRNITD

NHGKNKTTVHGYFSSIFLGGVDSLVDLMNKSFPELGIKKTDCKELSWIDT

TIFYSGVVNYNTANFKKEILLDRSAGKKTAFSIKLDYVKKLIPETAMVKI

LEKLYEEEVGVGMYVLYPYGGIMDEISESAIPFPHRAGIMYELWYTATWE

KQEDNEKHINWVRSVYNFTTPYVSQNPRLAYLNYRDLDLGKTNPESPNNY

TQARIWGEKYFGKNFNRLVKVKTKADPNNFFRNEQSIPPLPPRHH

Example 2: Cloning and Expression of CBCAS

CBCAS was amplified from a cannabis genomic DNA fragment using the primers 5'-CTGCAGGAATGAATT-GCTCAACATTCTCCT-3' (SEQ ID NO: 3) AND 5'-AAGCTTTCATGGTACCCCATGATGACGCGGTG-GAAGA-3' (SEQ ID NO: 4). The 50 µL reaction contained 100 ng of template, 0.2 µM of each primer, Pfu Ultrall DNA polymerase, 1× Pfu reaction buffer and 0.4 µM dNTPs. The cycling conditions were 95° C. for 20 s, 55° C. for 20 s, and 75° C. for 2 min. The product was purified, A-tailed with Taq polymerase, and cloned into pCR8/GW/TOPO entry vector (Invitrogen). Individual colonies were isolated, grown in LB media supplemented with spectinomycin, plasmid DNA was isolated using a Qiagen QiaPrep kit and verified by Sanger sequencing. The CBCAS ORF was excised using PstI and KpnI, isolated by gel electrophoresis, and cloned into IPICzαC (Invitrogen) that had been cut with the same restriction enzymes and dephosphorylated. The entire CBCA synthase coding sequence, including the native N-terminal secretory signal, was used in the construction of the Pichia expression vector.

The enzyme was expressed as an N-terminal fusion product with the vector encoded alpha-factor signal peptide to ensure protein secretion from the Pichia cells. IPICzαC: CBCAS was transformed into Pichia pastoris strain X33 (Invitrogen) by electroporation. Phleomycin-resistant colonies were selected and streaked onto minimal methanol plates, from which single colonies were picked and used to inoculate 50 mL of modified BMGY medium (1% yeast extract, 2% peptone, 50 mP HEPES pH 6, 1.34% yeast nitrogen base, $4 \times 10^{-5}$% biotin, 1% glycerol) which was grown for two days. Approximately 20 mL of this culture was used to inoculate 400 mL of modified BMMY medium (1% yeast extract, 2% peptone, 50 mM HEPES pH 7, 1.34% yeast nitrogen base, $4 \times 10^{-5}$% biotin, 1% methanol, 0.0001% riboflavin) to an approximate initial OD600 of 1. The culture was grown for four days at 20° C. with shaking at 90 RPM. Methanol was added every 24 h to a final concentration of 1%. After four days, the cells were removed from the medium by centrifugation (13k g for 20 min) and the clarified medium was passed through a 2 µm filter and stored on ice. 100 mL was passed through hydroxyapatite cartridge (BioRad Bio-Scale Mini CHT Type 1, 40 µm media) at 90 mL $h^{-1}$ that had been previously equilibrated with 5 CV of 10 mM sodium phosphate pH 7. Two cartridges were processed as such in parallel. The cartridges were washed with 5 column volumes of 10 mM sodium phosphate pH 7, and were then installed in series of an FLCP system (Akta, Amersham Biosciences). Proteins were eluted from the cartridges with a linear gradient of 10 mM sodium phosphate pH 7 to 100% 500 mM sodium phosphate pH over 7 over 20 column volumes at a flow rate of 1.75 mL $min^{-1}$. Five mL fractions were collected. After re-equilibrating the hydroxyapatite cartridges, the remaining medium was processed as above, and the fractions were then pooled and tested for CBCAS activity.

Example 3: CBCAS Assays

Reactions using media were performed by incubating 10 µmols CBGA in 500 µL of clarified culture media for 14 h. Reactions using hydroxyl-apatite fractions were performed with 100 µL of the fraction incubated with 10 nmols of CBGA for 14 h. Completed reactions were acidified with one drop of 4 N HCl and extracted twice with 400 µL of acetonitrile. After centrifugation, the organic phases were pooled and evaporated to dryness. Products were resuspended in 20 µL of 50% methanol, of which 10 µL was analyzed by LCMS. Products were separated with a Waters Alliance HPLC using a binary solvent system (solvent A: 10% acetonitrile, 0.05% formic acid; solvent B: 99.95% acetonitrile, 0.05% formic acid) and an Ascnetis C18 5 cm×2.1 mm 2.7 µm column (Sigma). Initial conditions: 55% A at 0.25 mL/min. Ramp to 5% A from 0-8 min, hold at 5% A for 2.5 min, return to initial conditions over 2 min and equilibrate at initial conditions for 7 min. Ultraviolet spectra were obtained using photodiode array detection at 200-350 nm.

Figure 2:
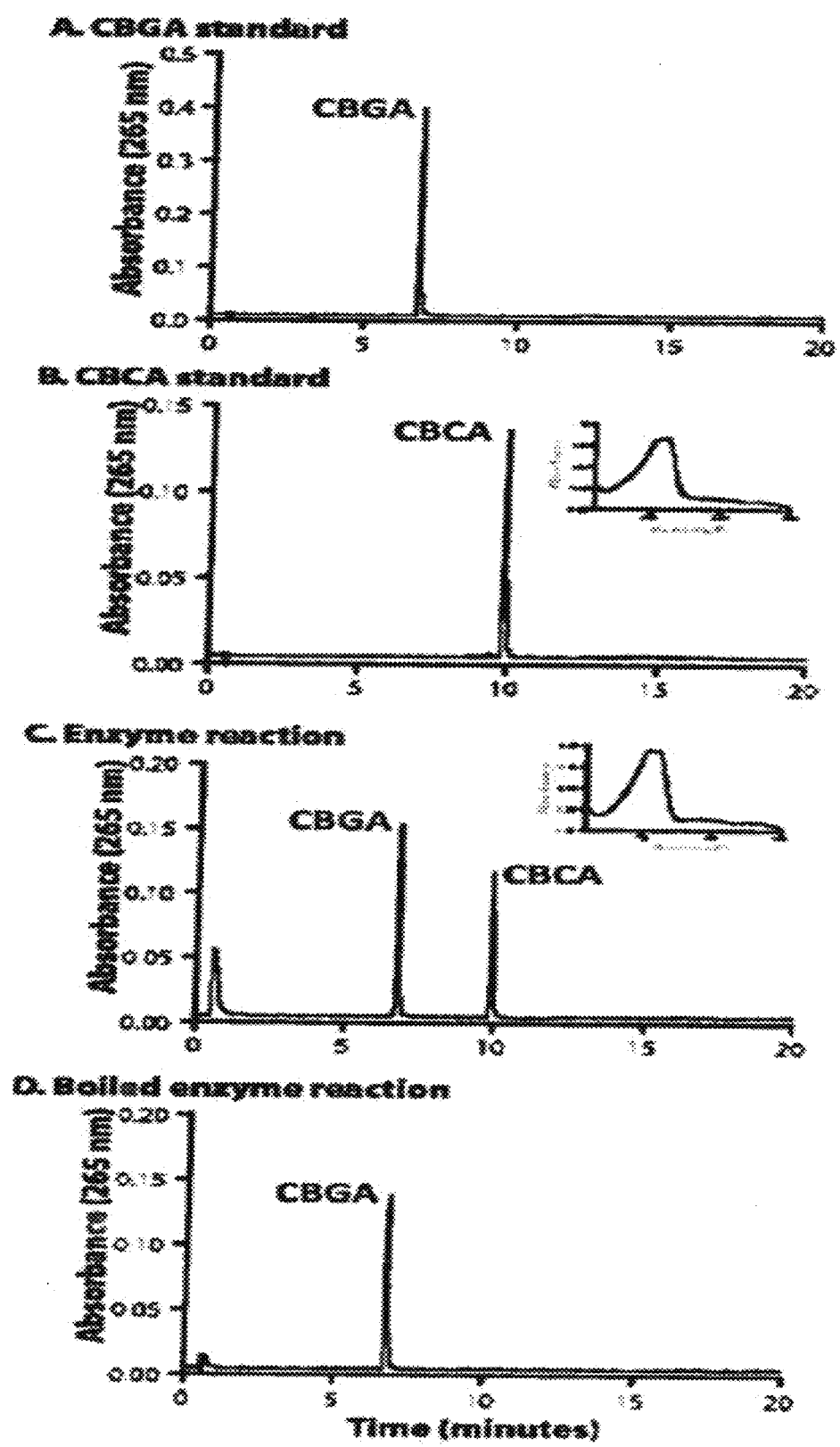
FIG. 2 depicts HPLC chromatograms of genuine cannabinoid standards and CBCAS reactions products. A. CBGA standard (retention time 6.8 min). B. CBCA standard (retention time 9.9 min). Inset is the ultraviolet spectrum of the CBCA standard. C. Products of CBCAS reaction showing that the recombinant enzyme produces CBCA (retention time 9.9 min). Inset is the ultraviolet spectrum of the CBCA produced by this reaction. D. Boiled enzyme reaction. No CBCA was produced by this reaction.
Figure 3:
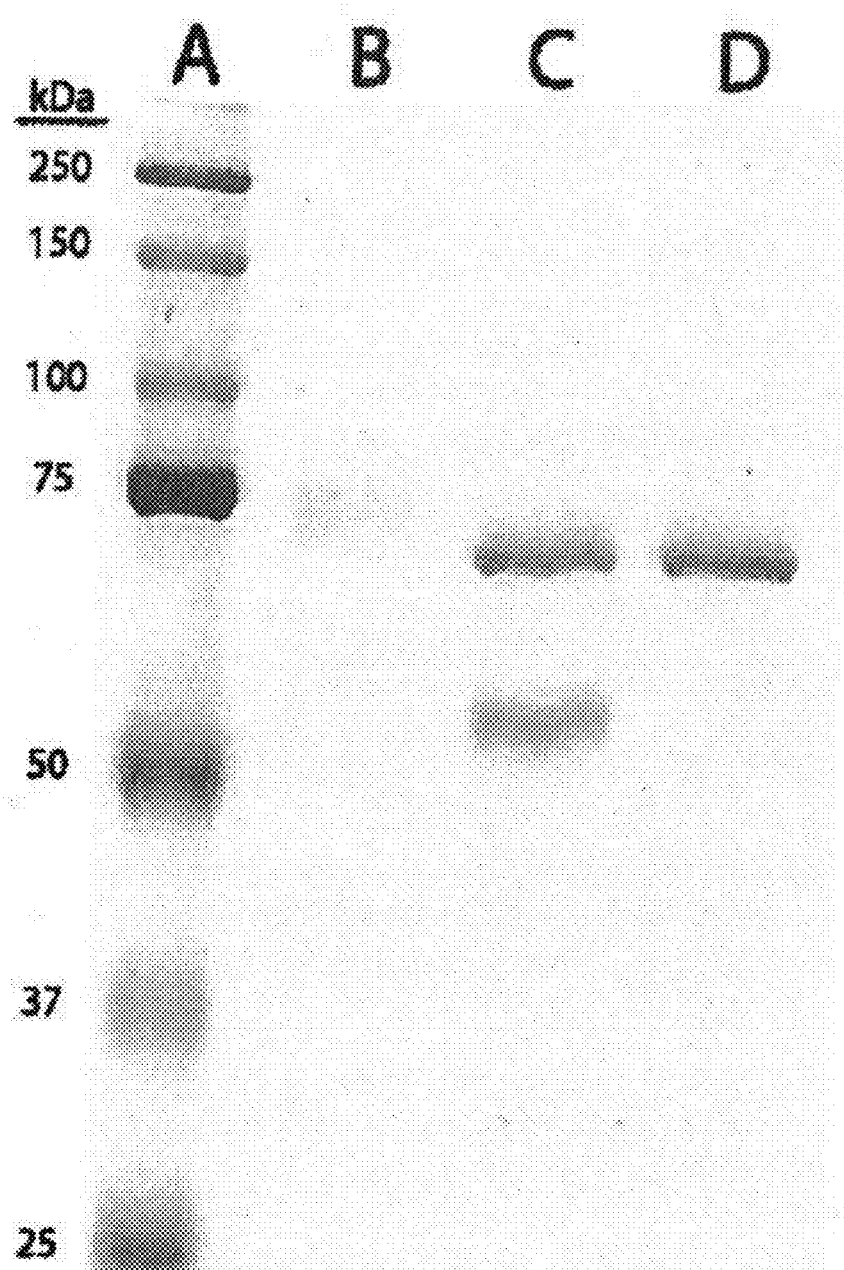
FIG. 3 depicts a SDS-PAGE gel or purified recombinant CBCAS expressed in *Pichia pastoris*. Panel A is the protein ladder. Panel B shows purified CBCAS. Panel C shows purified CBCAS deglycosylated with Endo Hf. The upper band shows Endo Hf (70 kDa), the lower band shows deglycosylated CBCAS (63 kDa). Panel D shows Endo Hf only.
Figure 4:
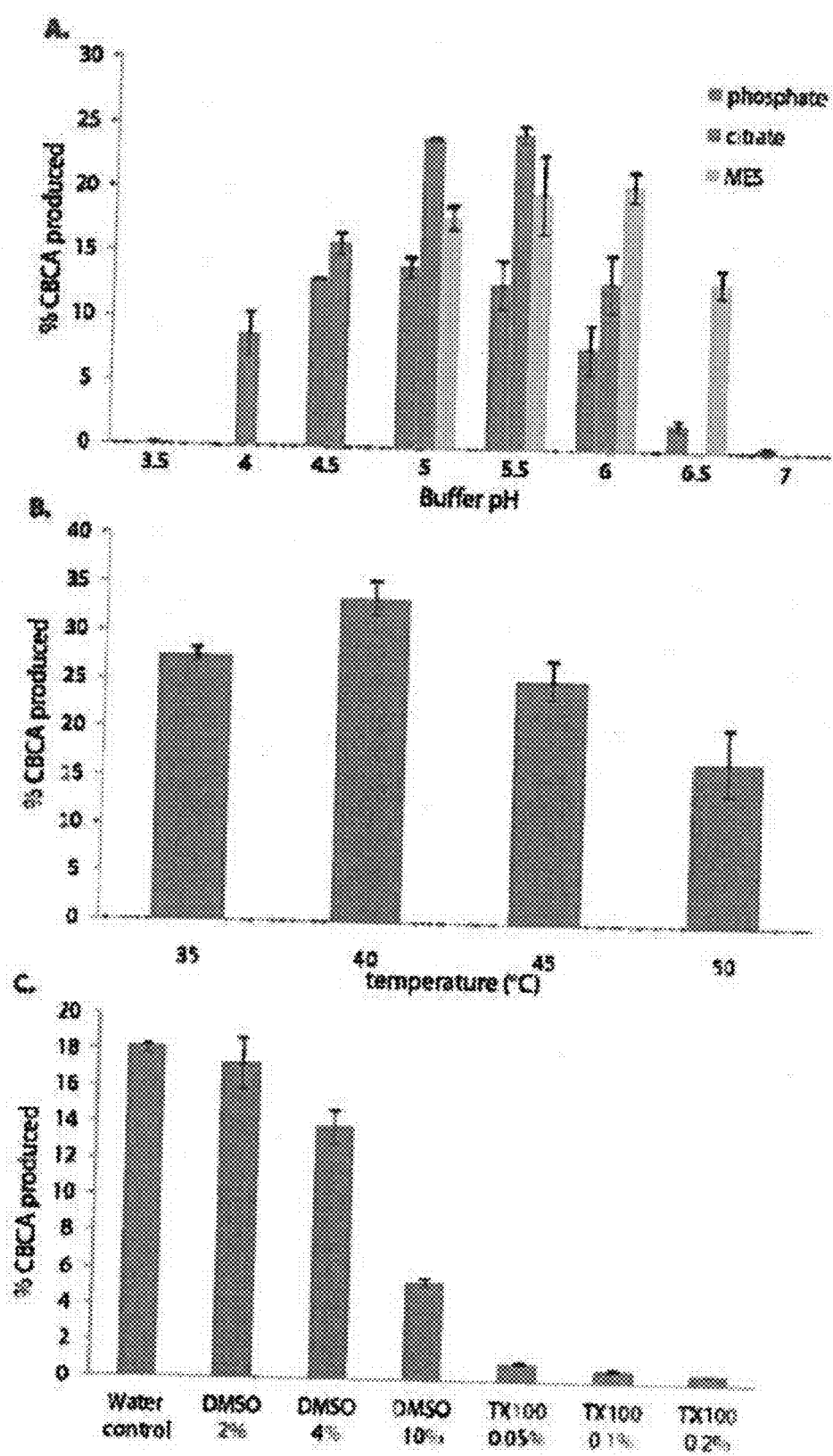
FIG. 4 depicts optimal conditions for CBCAS activity. Panel A shows the effect of a buffer and a buffer pH on CBCA production. Values are expressed as a fraction of CBCA produced (CBCA A265 nm/(CBGA A265 nm+CBCA A265 nm)*100). Panel B shows the effect of incubation temperature on CBCA production. Panel C shows the effect of additive on CBCA production.

As shown in FIG. 2, recombinant CBCAS catalyzed the formation of CBCA from CBGA. As shown in FIG. 3, the recombinant CBCAS has an apparent mass of 63 kDa after treatment with endoglycosylase (Endo Hf). As shown in FIG. 4, recombinant CBCAS has a pH optimum of 5.5, a temperature optimum of 40 degrees and is inhibited by high concentrations of DMSO and Triton X-100.

Activity for pH 3.5, 4, 4.5, 5, 5.5, 6, 6.5, and 7 were tested. There was activity between pH 4 and pH 6.5 in one or more buffers. Maximal activity was observed at pH 5 and 5.5. Activity for temperatures 35, 40, 45, and 50° C. were tested, with maximal activity observed at 40° C.

The present gene encodes a CBCAS enzyme from cannabis. This gene could be used to create, through breeding of recombinant plants, targeted mutagenesis, or genetic engineering, cannabis plants with enhanced cannabinoid production. In addition, inactivating or silencing this gene in cannabis could be used to block cannabinoid biosynthesis and thereby reduce production of cannabinoids such as CBCA, the precursor of CBC, in cannabis plants (e.g. industrial hemp). This gene could be used, in combination with genes encoding other enzymes in the cannabinoid pathway, to engineer cannabinoid biosynthesis in other plants or in microorganisms.

Example 4

Recombinant sequences lacking predicted signal sequence and comprising a start codon/start methionine SEQ ID NO: 5
ATG---------------------------------------------
-------------------------------------CCTCAAGAAAACT
TCCTTAAATGCTTCTCGGAATATATTCCTAACAATCCAGCAAATCCAAA
TTCATATACACTCAACACGACCAATTGTATATGTCTGTCCTGAATTCGAC
AATACAAAATCTTAGATTCACCTCTGATACAACCCCAAAACCACTCGTTA
TTGTCACTCCTTCAAATGTCTCCCATATCCAGGCCAGTATTCTCTGCTCC
AAGAAAGTTGGTTTGCAGATTCGAACTCGAAGCGGTGGCCATGATGCTGA
GGGTTTGTCCTACATATCTCAAGTCCCATTTGCTATAGTAGACTTGAGAA
ACATGCATACGGTCAAAGTAGATATTCATAGCCAAACTGCGTGGGTTGAA
GCCGGAGCTACCCTTGGAGAAGTTTATTATTGGATCAATGAGATGAATGA
GAATTTTAGTTTTCCTGGTGGGTATTGCCCTACTGTTGGCGTAGGTGGAC
ACTTTAGTGGAGGAGGCTATGGAGCATTGATGCGAAATTATGGCCTTGCG
GCTGATAATATCATTGATGCACACTTAGTCAATGTTGATGGAAAAGTTCT
AGATCGAAAATCCATGGGAGAAGATCTATTTTGGGCTATACGTGGTGGAG
GAGGAGAAAACTTTGGAATCATTGCAGCATGTAAAATCAAACTTGTTGTT
GTCCCATCAAAGGCTACTATATTCAGTGTTAAAAAGAACATGGAGATACA
TGGGCTTGTCAAGTTATTTAACAAATGGCAAAATATTGCTTACAAGTATG
ACAAAGATTTAATGCTCACGACTCACTTCAGAACTAGGAATATTACAGAT
AATCATGGGAAGAATAAGACTACAGTACATGGTTACTTCTCTTCCATTTT
TCTTGGTGGAGTGGATAGTCTAGTTGACTTGATGAACAAGAGCTTTCCTG
AGTTGGGTATTAAAAAAACTGATTGCAAAGAATTGAGCTGGATTGATACA
ACCATCTTCTACAGTGGTGTTGTAAATTACAACACTGCTAATTTTAAAAA
GGAAATTTTGCTTGATAGATCAGCTGGGAAGAAGACGGCTTTCTCAATTA
AGTTAGACTATGTTAAGAAACTAATACCTGAAACTGCAATGGTCAAAATT
TTGGAAAAATTATATGAAGAAGAGGTAGGAGTTGGGATGTATGTGTTGTA
CCCTTACGGTGGTATAATGGATGAGATTTCAGAATCAGCAATTCCATTCC
CTCATCGAGCTGGAATAATGTATGAACTTTGGTACACTGCTACCTGGGAG
AAGCAAGAAGATAACGAAAAGCATATAAACTGGGTTCGAAGTGTTTATAA
TTTCACAACTCCTTATGTGTCCCAAAATCCAAGATTGGCGTATCTCAATT
ATAGGGACCTTGATTTAGGAAAAACTAATCCTGAGAGTCCTAATAATTAC
ACACAAGCACGTATTTGGGTGAAAAGTATTTTGGTAAAAATTTTAACAG
GTTAGTTAAGGTGAAAACCAAAGCTGATCCCAATAATTTTTTTAGAAACG
AACAAAGTATCCCACCTCTTCCACCGCGTCATCAT
- dashes represent deleted sequence SEQ ID NO: 6
M------------------------NPQENFLKCFSEYIPNNPANPK
FIYTQHDQLYMSVLNSTIQNLRFTSDTTPKPLVIVTPSNVSHIQASILCS
KKVGLQIRTRSGGHDAEGLSYISQVPFAIVDLRNMHTVKVDIHSQTAWVE
AGATLGEVYYWINEMNENFSFPGGYCPTVGVGGHFSGGGYGALMRNYGLA
ADNIIDAHLVNVDGKVLDRKSMGEDLFWAIRGGGGENFGIIAACKIKLVV
VPSKATIFSVKKNMEIHGLVKLFNKWQNIAYKYDKDLMLTTHFRTRNITD
NHGKNKTTVHGYFSSIFLGGVDSLVDLMNKSFPELGIKKTDCKELSWIDT
TIFYSGVVNYNTANFKKEILLDRSAGKKTAFSIKLDYVKKLIPETAMVKI
LEKLYEEEVGVGMYVLYPYGGIMDEISESAIPFPHRAGIMYELWYTATWE
KQEDNEKHINWVRSVYNFTTPYVSQNPRLAYLNYRDLDLGKTNPESPNNY
TQARIWGEKYFGKNFNRLVKVKTKADPNNFFRNEQSIPPLPPRHH Predicted N terminal signal peptide:
SEQ ID NO: 7
MNCSTFSFWFVCKIIFFFLSFNIQISIA

Example 5

Codon optimized sequences were generated for *E. coli* and yeast.

*E. coli* Optimized sequence

SEQ ID NO: 8)
ATGAACTGCT CGACATTTAG TTTTTGGTTT GTGTGCAAGA
TCATTTTTTT TTTTCTTTCG TTTAACATTC AGATTAGTAT
TGCAAACCCG CAGGAGAACT TTCTCAAATG TTTTAGCGAA
TATATCCCGA CAACCCGGC CAACCCGAAA TTCATTTACA
CACAACACGA TCAACTGTAC ATGAGCGTAT TGAACAGCAC
CATCCAGAAT TTGCGCTTTA CTTCGGACAC AACGCCGAAG
CCTCTGGTCA TCGTTACGCC CTCGAATGTT TCACATATCC
AAGCGTCAAT TCTTTGTTCT AAAAAGGTCG GCCTGCAGAT
TCGCACACGG TCGGGCGGCC ATGATGCCGA AGGTCTGTCT
TACATCTCAC AAGTCCCTTT CGCAATCGTT GATTTGCGGA
ACATGCACAC TGTAAAAGTT GATATTCACT CACAAACCGC
TTGGGTCGAA GCAGGTGCCA CGCTTGGGGA AGTATATTAC
TGGATTAACG AAATGAACGA GAATTTCTCG TTTCCAGGCG
GTTACTGCCC AACCGTAGGT GTGGGCGGTC ATTTTTCCGG
AGGCGGTTAT GGTGCGTTAA TGCGCAACTA TGGCCTGGCG
GCAGACAATA TTATTGATGC CCACCTCGTT AATGTGGATG
GTAAAGTACT GGATCGCAAA TCAATGGGTG AAGACCTCTT
CTGGGCGATT CGTGGTGGGG GTGGCGAGAA CTTTGGTATC
ATCGCGGCAT GTAAGATCAA GCTGGTGGTA GTTCCGTCTA
AAGCGACCAT CTTTAGCGTG AAAAAAAACA TGGAGATTCA
CGGCCTGGTA AAATTGTTCA ACAAATGGCA GAACATCGCT
TACAAATACG ACAAAGATCT GATGTTAACG ACTCACTTCC
GCACCCGTAA CATTACTGAC AATCACGGCA AAAATAAGAC
TACTGTGCAT GGTTACTTTA GTAGTATCTT CCTGGGTGGA
GTCGATTCCC TGGTCGATTT AATGAACAAG AGCTTTCCGG

```
AGCTGGGGAT TAAAAAAACC GACTGTAAAG AGCTGAGTTG

GATCGACACG ACGATCTTCT ACAGCGGAGT AGTCAACTAC

AACACTGCCA ACTTTAAGAA AGAAATTCTG CTGGACCGCA

GCGCAGGTAA AAAGACCGCC TTCTCCATCA AACTGGATTA

CGTCAAAAAG CTGATTCCGG AAACAGCAAT GGTAAAGATT

CTGGAAAAAC TGTATGAAGA AGAGGTTGGC GTTGGCATGT

ATGTCTTATA TCCGTATGGG GGCATTATGG ATGAAATTTC

TGAAAGTGCT ATTCCCTTCC CACACCGCGC GGGGATTATG

TACGAACTGT GGTATACGGC CACGTGGGAA AAACAAGAGG

ACAATGAGAA ACACATCAAC TGGGTTCGGT CAGTATATAA

CTTTACCACC CCGTATGTCT CGCAGAACCC GCGTCTGGCG

TATCTGAACT ATCGCGATCT TGATTTGGGT AAAACCAATC

CGGAAAGCCC GAATAACTAC ACCCAGGCAC GCATTTGGGG

GGAAAAATAT TTCGGGAAAA ACTTCAACCG GCTGGTGAAG

GTGAAAACGA AGGCTGACCC GAATAACTTT TTTCGGAATG

AACAAAGCAT TCCGCCGTTA CCGCCGCGCC ACCAC
```

The *E. coli* optimized sequence shares 75% sequence identity with SEG ID NO: 1

*Saccharomyces* (yeast) Optimized sequence (SEQ ID NO: 9)
```
ATGAATTGTA GTACTTTCTC TTTCTGGTTT GTTTGTAAGA

TTATATTTTT TTTTCTTAGT TTCAATATAC AAATTTCAAT

TGCAAACCCT CAAGAAAATT TCCTTAAGTG CTTTTCAGAA

TATATCCCTA ATAATCCTGC AAACCCTAAA TTCATTTATA

CACAACATGA TCAGTTATAT ATGTCTGTCT TAAACTCTAC

CATTCAAAAT TTGAGGTTCA CGTCTGATAC AACCCCAAAG

CCTTTAGTTA TCGTGACACC CTCTAACGTT AGTCATATTC

AGGCTAGTAT CTTATGTTCA AAAAAGTGG GTTTACAAAT

CAGAACTAGG TCTGGTGGTC ATGACGCGGA AGGTCTGTCT

TACATATCTC AGGTGCCGTT TGCAATCGTT GATCTACGTA

ATATGCATAC AGTTAAAGTC GATATTCACT CTCAAACTGC

ATGGGTCGAG GCTGGTGCCA CTCTAGGTGA AGTTTATTAC

TGGATCAATG AAATGAACGA GAATTTTTCC TTCCCAGGTG

GTTATTGTCC TACTGTGGGT GTAGGCGGAC ACTTTTCTGG

CGGGGGGTAT GGTGCTTTGA TGAGGAACTA TGGTTTGGCC

GCCGATAATA TAATTGACGC CCATCTTGTA AACGTCGACG

GGAAGGTTCT GGACCGTAAA TCTATGGGTG AAGATTTATT

CTGGGCGATA AGAGGTGGCG GGGAGAGAA CTTTGGTATT

ATCGCAGCTT GTAAGATTAA GTTAGTTGTT GTCCCCTCAA

AAGCAACAAT TTTTTCAGTG AAGAAGAACA TGGAAATCCA

CGGTTTGGTA AAACTGTTTA ATAAATGGCA GAATATTGCC
```
```
TACAAATACG ATAAGGATTT GATGTTGACA ACACATTTCA

GAACTAGAAA TATTACTGAC AACCACGGAA AGAACAAGAC

AACCGTCCAT GGATATTTTA GTTCTATTTT CTTAGGCGGA

GTTGATTCAC TAGTAGACTT AATGAACAAG TCTTTCCCCG

AATTGGGAAT AAAAAAAACC GATTGCAAGG AATTATCCTG

GATAGATACA ACAATATTCT ACTCTGGAGT CGTTAATTAT

AATACGGCCA ACTTTAAGAA GGAAATATTA TTAGATCGTT

CCGCAGGTAA AAAGACAGCT TTTTCCATAA AATTGGACTA

CGTCAAAAAA TTAATTCCTG AGACAGCCAT GGTAAAAATA

TTGGAAAAAT TGTACGAAGA GGAGGTAGGC GTGGGTATGT

ATGTGTTATA CCCATACGGT GGTATTATGG ATGAAATTTC

TGAGAGCGCT ATTCCCTTCC CCCATCGTGC AGGTATAATG

TATGAATTAT GGTACACAGC AACATGGGAA AAACAAGAGG

ATAACGAAAA GCATATTAAT TGGGTACGTA GTGTGTACAA

CTTTACGACA CCTTACGTGT CCCAAAATCC AAGATTAGCG

TATTTGAACT ATAGAGACTT AGATTTAGGT AAAACAAACC

CTGAGTCTCC AAATAATTAC ACCCAAGCCA GGATTTGGGG

TGAAAAATAC TTCGGCAAAA ATTTCAATAG ATTGGTTAAG

GTAAAAACTA AGGCGGATCC AAACAATTTT TTTAGAAATG

AGCAGAGTAT TCCGCCCCTG CCTCCAAGAC ACCAT
```

The yeast optimized sequence shares 78% sequence identity with SEQ ID NO:1.

Other advantages that are inherent to the structure are obvious to one skilled in the art. The embodiments are described herein illustratively and are not meant to limit the scope of the invention as claimed. Variations of the foregoing embodiments will be evident to a person of ordinary skill and are intended by the inventor to be encompassed by the following claims.

REFERENCES

Alvarez J P, Pekker I, Goldshmidt A, Blum E, Amsellem Z, Eshed Y (2006) Endogenous and synthetic microRNAs stimulate simultaneous, efficient, and localized regulation of multiple targets in diverse species. *Plant Cell* 18:1134-51.

van Bakel, H., Stout, J. M., Cote, A. G., Tallon, C. M., Sharpe, A. G., Hughes, T. R., & Page, J. E. (2011). The draft genome and transcriptome of *Cannabis sativa*. *Genome Biology*, 12(10), R102.

Bechtold N, Ellis J, Pelletier G (1993) In planta *Agrobacterium*-mediated gene transfer by infiltration of adult *Arabidopsis thaliana* plants. *C R Acad Sci Paris, Sciences de la vie/Life sciences* 316: 1194-1199.

Becker D, Brettschneider R, Lorz H (1994) Fertile transgenic wheat from microprojectile bombardment of scutellar tissue. *Plant J.* 5: 299-307.

Bourrie, M (2003) Hemp: *A Short History of the Most Misunderstood Plant and Its Uses and Abuses* (Key Porter, Toronto).

Collakova E, DellaPenna D (2001) Isolation and functional analysis of homogentisate phytyltransferase from *Synechocystis* sp. PCC 6803 and *Arabidopsis*. *Plant Physiol* 127: 1113-1124.

Datla R, Anderson J W, Selvaraj G (1997) Plant promoters for transgene expression. *Biotechnology Annual Review* 3: 269-296.

Davis, W. M., & Hatoum, N. S. (1983). Neurobehavioral actions of cannabichromene and interactions with delta 9-tetrahydrocannabinol. *General Pharmacology*, 14(2), 247-52.

DeBlock M, DeBrouwer D, Tenning P (1989) Transformation of *Brassica napus* and *Brassica oleracea* using *Agrobacterium tumefaciens* and the expression of the bar and neo genes in the transgenic plants. *Plant Physiol.* 91: 694-701.

DeLong, G. T., Wolf, C. E., Poklis, A., & Lichtman, A. H. (2010). Pharmacological evaluation of the natural constituent of *Cannabis sativa*, cannabichromene and its modulation by Δ(9)-tetrahydrocannabinol. *Drug and Alcohol Dependence*, 112(1-2), 126-33.

Depicker A, Montagu M V (1997) Post-transcriptional gene silencing in plants. *Curr Opin Cell Biol.* 9: 373-82.

Elsohly, M. A., & Slade, D. (2005). Chemical constituents of marijuana: the complex mixture of natural cannabinoids. *Life Sciences*, 78(5), 539-48.

Feeney M and Z K Punja (2003) Tissue culture and *Agrobacterium*-mediated transformation of Hemp (*Cannabis sativa* L.) In Vitro Cell Dev Biol-Plant 39:578-585

Fellermeier M, Zenk M H. (1998) Prenylation of olivetolate by a hemp transferase yields cannabigerolic acid, the precursor of tetrahydrocannabinol. *FEBS Letters.* 427: 283-285.

Fernandez-Valverde, M., Reglero, A., Martinez-Blanco, H., & Luengo, J. M. (1993). Purification of Pseudomonas putida acyl coenzyme A ligase active with a range of aliphatic and aromatic substrates. *Appl. Envir. Microbiol.*, 59(4), 1149-1154.

Gagne, S. J., Stout, J. M., Liu, E., Boubakir, Z., Clark, S. M., & Page, J. E. (2012). Identification of olivetolic acid cyclase from *Cannabis sativa* reveals a unique catalytic route to plant polyketides. *Proceedings of the National Academy of Sciences of the United States of America*, 109(31), 12811-6.

Helliwell C A, Waterhouse P M (2005) Constructs and methods for hairpin RNA-mediated gene silencing in plants. *Methods Enzymology* 392:24-35.

Izzo, A. A., Capasso, R., Aviello, G., Borrelli, F., Romano, B., Piscitelli, F., . . . Di Marzo, V. (2012). Inhibitory effect of cannabichromene, a major non-psychotropic cannabinoid extracted from *Cannabis sativa*, on inflammation-induced hypermotility in mice. *British Journal of Pharmacology*, 166(4), 1444-60.

Henikoff S, Till B J, Comai L (2004) TILLING. Traditional mutagenesis meets functional genomics. *Plant Physiol* 135:630-6.

Katavic V, Haughn G W, Reed D, Martin M, Kunst L (1994) In planta transformation of *Arabidopsis thaliana. Mol. Gen. Genet.* 245: 363-370.

Katsuyama Y, Funa N, Miyahisa I, Horinouchi S (2007) Synthesis of unnatural flavonoids and stilbenes by exploiting the plant biosynthetic pathway in *Escherichia coli. Chem Biol.* 14(6): 613-21.

Kichikai K, Taura F, Morimoto S, Masayama Y. (2001) Japanese Patent Publication 2001-029082 published Feb. 6, 2001.

Kojoma M, Seki H Yoshida S Muranaka T (2006) DNA polymorphisms in the THCA synthase gene in "drug-type" and "figer-type" *Cannabis sativa* L. Forensic Sci Int 159: 132-40.

Leonard E, Yan Y, Fowler Z L, Li Z, Lim C G, Lim K H, Koffas M A (12 Mar. 2008) Strain Improvement of Recombinant *Escherichia coli* for Efficient Production of Plant Flavonoids. *Mol Pharm.* [Epub ahead of print] PMID: 18333619 [PubMed—as supplied by publisher].

Ligresti, A., Moriello, A. S., Starowicz, K., Matias, I., Pisanti, S., De Petrocellis, L., . . . Di Marzo, V. (2006). Antitumor activity of plant cannabinoids with emphasis on the effect of cannabidiol on human breast carcinoma. *Journal of Pharmacology and Experimental Therapeutics*, 318 (3), 1375-87. doi:10.1124/jpet.106.105247

Maione, S., Piscitelli, F., Gatta, L., Vita, D., De Petrocellis, L., Palazzo, E., . . . Di Marzo, V. (2011). Non-psychoactive cannabinoids modulate the descending pathway of antinociception in anaesthetized rats through several mechanisms of action. *British Journal of Pharmacology*, 162(3), 584-96. doi:10.1111/j.1476-5381.2010.01063.x Meyer P (1995) Understanding and controlling transgene expression. *Trends in Biotechnology*, 13: 332-337.

Moloney M M, Walker J M, Sharma K K (1989) High efficiency transformation of *Brassica napus* using *Agrobacterium* vectors. *Plant Cell Rep.* 8: 238-242.

Morimoto S, Komatsu K, Taura F, Shoyama, Y. (1998) Purification and characterization of cannabichromenic acid synthase from *Cannabis sativa. Phytochemistry.* 49: 1525-1529.

Nehra N S, Chibbar R N, Leung N, Caswell K, Mallard C, Steinhauer L, Baga M, Kartha K K (1994) Self-fertile transgenic wheat plants regenerated from isolated scutellar tissues following microprojectile bombardment with two distinct gene constructs. *Plant J.* 5: 285-297.

Ohyanagi H, Tanaka T, Sakai H, Shigemoto Y, Yamaguchi K, Habara T, Fujii Y, Antonio B A, Nagamura Y, Imanishi T, Ikeo K, Itoh T, Gojobori T, Sasaki T. (2008) GenBank Accession NP_001060083.

Page J E, Nagel J (2006) Biosynthesis of terpenophenolics in hop and cannabis. In J T Romeo, ed, *Integrative Plant Biochemistry*, Vol. 40. Elsevier, Oxford, pp 179-210.

R. G. Pertwee, R. G. Pertwee, Cannabinoids R. G. Pertwee, Ed. (Springer-Verlag, Berlin/Heidelberg, 2005), pp. 1-51-51.

Potrykus I (1991) Gene transfer to plants: Assessment of published approaches and results. Annu. Rev. Plant Physiol. *Plant Mol. Biol.* 42: 205-225.

Pouwels et al., *Cloning Vectors. A Laboratory Manual*, Elsevier, Amsterdam (1986).

Ralston L, Subramanian S, Matsuno M, Yu O (2005) Partial reconstruction of flavonoid and isoflavonoid biosynthesis in yeast using soybean type I and type II chalcone isomerases. *Plant Physiol.* 137(4): 1375-88.

Rhodes C A, Pierce D A, Mettler I J, Mascarenhas D, Detmer J J (1988) Genetically transformed maize plants from protoplasts. *Science* 240: 204-207.

Romano, B., Borrelli, F., Fasolino, I., Capasso, R., Piscitelli, F., Cascio, M., . . . Izzo, A. (2013). The cannabinoid TRPA1 agonist cannabichromene inhibits nitric oxide production in macrophages and ameliorates murine colitis. *British Journal of Pharmacology*, 169(1), 213-29.

Sambrook et al, *Molecular Cloning: A Laboratory Manual, Third Edition*, Cold Spring Harbor, N.Y. (2001).

Sanford J C, Klein T M, Wolf E D, Allen N (1987) Delivery of substances into cells and tissues using a particle bombardment process. *J. Part. Sci. Technol.* 5: 27-37.

Schneider, K., Kienow, L., Schmelzer, E., Colby, T., Bartsch, M., Miersch, O., . . . Stuible, H.-P. (2005). A new type of peroxisomal acyl-coenzyme A synthetase from *Arabidopsis thaliana* Has the Catalytic Capacity to Activate Biosynthetic Precursors of Jasmonic Acid 10.1074/jbc. M413578200. *Journal of Biological Chemistry,* 280(14), 13962-13972.

Schwab R, Ossowski S, Riester M, Warthmann N, Weigel D (2006) Highly specific gene silencing by artificial microRNAs in *Arabidopsis. Plant Cell* 18:1121-33.

Shimamoto K, Terada R, Izawa T, Fujimoto H (1989) Fertile transgenic rice plants regenerated from transformed protoplasts. *Nature* 338: 274-276.

Shockey, J. M., Fulda, M. S., & Browse, J. (2003). Arabidopsis Contains a Large Superfamily of Acyl-Activating Enzymes. Phylogenetic and Acyl-Coenzyme A Synthetases. *Plant Physiol.,* 132(June), 1065-1076.

Shoyama Y, Hirano H, Nishioka I. (1984) Biosynthesis of propyl cannabinoid acid and its biosynthetic relationship with pentyl and methyl cannabinoid acids. *Phytochemistry.* 23(9): 1909-1912.

Sirikantaramas S, Morimoto S, Shoyama Y, Ishikawa Y, Wada Y, Shoyama Y, Taura F. (2004) The gene controlling marijuana psychoactivity: molecular cloning and heterologous expression of Delta1-tetrahydrocannabinolic acid synthase from *Cannabis sativa* L. *J Biol Chem.* 279: 39767-39774.

Sirikantaramas S, Taura F, Tanaka Y, Ishikawa Y, Morimoto S, Shoyama Y. (2005) Tetrahydrocannabinolic acid synthase, the enzyme controlling marijuana psychoactivity, is secreted into the storage cavity of the glandular trichomes. *Plant Cell Physiol.* 46: 1578-1582.

Songstad D D, Somers D A, Griesbach R J (1995) Advances in alternative DNA delivery techniques. *Plant Cell, Tissue and Organ Culture* 40:1-15.

Stam M, de Bruin R, van Blokland R, van der Hoorn R A, Mol J N, Kooter J M (2000) Distinct features of posttranscriptional gene silencing by antisense transgenes in single copy and inverted T-DNA repeat loci. *Plant J.* 21:27-42.

Stout, J. M., Boubakir, Z., Ambrose, S. J., Purves, R. W., & Page, J. E. (2012). The hexanoyl-CoA precursor for cannabinoid biosynthesis is formed by an acyl-activating enzyme in *Cannabis sativa* trichomes. *Plant J.* 71(3): 353-65.

Taura F, Morimoto S, Shoyama Y. (1996) Purification and characterization of cannabidiolic-acid synthase from *Cannabis sativa* L. Biochemical analysis of a novel enzyme that catalyzes the oxidocyclization of cannabigerolic acid to cannabidiolic acid. *J Biol Chem.* 271: 17411-17416.

Taura F, Morimoto S, Shoyama Y, Mechoulam R. (1995) First direct evidence for the mechanism of 1-tetrahydrocannabinolic acid biosynthesis. *Journal of the American Chemical Society.* 117: 9766-9767.

Taura F, Matsushita H, Morimoto S, Masayama Y. (2000) Japanese Patent Publication 2000-078979 published Mar. 21, 2000.

Taura F, Sirikantaramas S, Shoyama Y, Yoshikai K, Shoyama Y, Morimoto S. (2007) Cannabidiolic-acid synthase, the chemotype-determining enzyme in the fiber-type *Cannabis sativa. FEBS Left.* 581: 2929-2934.

Taura F, Tanaka S, Taguchi C, Fukamizu T, Tanaka H, Shoyama Y, Morimoto, S. (2009) Characterization of olivetol synthase, a polyketide synthase putatively involved in cannabinoid biosynthetic pathway. *FEBS Left.* 583: 2061-2066.

Vasil I K (1994) Molecular improvement of cereals. *Plant Mol. Biol.* 25: 925-937.

Veress T, Szanto J. I. and Leisztner, L (1990) Determination of cannabinoid acids by high performance liquied chromatography of their neutral derivatives formed by thermal decarboxylation. *J. of Chromatography,* 520:339-347

Walden R, Wingender R (1995) Gene-transfer and plant regeneration techniques. *Trends in Biotechnology* 13: 324-331.

Ware, M. A., Wang, T., Shapiro, S., Robinson, A., Ducruet, T., Huynh, T., . . . Collet, J.-P. (2010). Smoked cannabis for chronic neuropathic pain: a randomized controlled trial. CMAJ: Canadian Medical Association Journal=*Journal de l'Association Medicale Canadienne,* 182(14), E694-701.

Wirth, P. W., Watson, E. S., ElSohly, M. A., Seidel, R., Murphy, J. C., & Turner, C. E. (1980). Anti-inflammatory activity of cannabichromene homologs. *Journal of Pharmaceutical Sciences,* 69(11), 1359-60.

Zhang H, Wang Y, Pfeifer B A (31 Jan. 2008) Bacterial hosts for natural product production. *Mol Pharm.* [Epub ahead of print] PMID: 18232637 [PubMed—as supplied by publisher].

We claim:

1. A nucleic acid molecule comprising:
    i) a cDNA having a nucleotide sequence encoding a polypeptide having the sequence set forth in SEQ ID NO: 2 or 6 or a polypeptide having at least 99.5% sequence identity to SEQ ID NO: 2 or 6 and encoding a polypeptide having cannabichromenic acid synthase activity;
    ii) a cDNA having a nucleotide sequence having at least, greater than or about 99.5% sequence identity to SEQ ID NO: 1 or 5 and encoding a polypeptide having cannabichromenic acid synthase activity;
    iii) a cDNA having a nucleotide sequence having at least, greater than or about 90% sequence identity to SEQ ID NO: 8 or 9 and encoding a polypeptide having cannabichromenic acid synthase activity; or
    iv) a nucleotide sequence that is the complement of i), ii).

2. The nucleic acid molecule of claim 1, wherein the nucleotide sequence is as set forth in SEQ ID NO: 1 or 5 or a codon degenerate nucleotide sequence thereof, optionally wherein the codon degenerate nucleotide sequence comprises the sequence set forth in SEQ ID NO: 8 or 9, or the complement of any of the foregoing.

3. The nucleic acid molecule of claim 1, wherein the encoded polypeptide has an amino acid sequence as set forth in SEQ ID NO: 2 or 6.

4. The nucleic acid molecule of claim 1, wherein the nucleic acid molecule is conjugated to or comprises one or more heterologous moieties, optionally one or more of a heterologous nucleic acid, a detectable label or a tag.

5. An in vitro expression system comprising a nucleic acid molecule comprising:
    i) a nucleotide sequence encoding a polypeptide having the sequence set forth in SEQ ID NO: 2 or 6 or a polypeptide having at least 99.5% sequence identity to SEQ ID NO: 2 or 6 and encoding a polypeptide having cannabichromenic acid synthase activity;
    ii) a nucleotide sequence having at least, greater than or about 99.5% sequence identity to SEQ ID NO: 1 or 5 and encoding a polypeptide having cannabichromenic acid synthase activity;

iii) a nucleotide sequence having at least, greater than or about 90% sequence identity to SEQ ID NO: 8 or 9 and encoding a polypeptide having cannabichromenic acid synthase activity; or iv) a nucleotide sequence that is the complement of i), ii) or iii).

6. A recombinant organism, cell or tissue comprising or produced using the nucleic acid molecule of claim 1.

7. The organism of claim 6, wherein the organism is a microorganism.

8. The organism of claim 7, wherein the microorganism is yeast or *E. coli*.

9. A composition comprising (a) the nucleic acid molecule according to claim 1; and/or a purified extract of a recombinant cell, organism or tissue comprising or produced with said nucleic acid molecule.

10. The nucleic acid molecule of claim 4, wherein the nucleic acid molecule encodes a polypeptide having the sequence set forth in SEQ ID NO: 6 or a polypeptide having at least 99.5% sequence identity to SEQ ID NO: 6 and the heterologous nucleic acid is a signal sequence, optionally alpha mating factor signal sequence, α-amylase signal sequence, glucoamylase signal sequence, serum albumin signal sequence, inulinase signal sequence, invertase signal sequence, killer protein signal sequence or lysozyme signal sequence.

11. The in vitro system of claim 5, wherein the nucleotide sequence is as set forth in SEQ ID NO: 1 or 5 or a codon degenerate nucleotide sequence thereof, optionally wherein the codon degenerate nucleotide sequence comprises the sequence set forth in SEQ ID NO: 8 or 9, or the complement of any of the foregoing.

12. The in vitro system of claim 5, wherein the amino acid sequence is as set forth in SEQ ID NO: 2 or 6.

13. The in vitro system of claim 5, wherein the nucleic acid molecule or the polypeptide is coupled to one or more heterologous moieties, optionally one or more of a linker, a signal sequence, a detectable label or a tag.

14. The in vitro system of claim 13, wherein the nucleic acid molecule encodes a polypeptide having the sequence set forth in SEQ ID NO: 6 or a polypeptide having at least 99.5% sequence identity to SEQ ID NO: 6 and the heterologous nucleic acid is a signal sequence, optionally alpha mating factor signal sequence, α-amylase signal sequence, glucoamylase signal sequence, serum albumin signal sequence, inulinase signal sequence, invertase signal sequence, killer protein signal sequence or lysozyme signal sequence.

15. The in vitro expression system of claim 5, further comprising one or more of a translation competent extract of whole cells, a RNA polymerase, one or more regulatory protein factors, one or more transcription factors, ribosome preparation, and tRNA.

16. The in vitro expression system of claim 5, wherein the nucleic acid molecule is comprised in a vector with 5' T7 promoter upstream of the nucleic acid molecule.

17. The in vitro expression system of claim 5, further comprising one or more other nucleic acids that encode one or more enzymes in a cannabinoid biosynthetic pathway.

18. The in vitro expression system of claim 5, wherein the one or more enzymes in a cannabinoid biosynthetic pathway is one or more of hexanoyl CoA synthetase, olivetolic acid cyclase, a THCA synthase, a CBDA synthase, or aromatic prenyltransferase PT1.

19. The organism, cell or tissue of claim 6, wherein the organism is a plant, the cell is a plant cell or the tissue is a plant germ tissue.

20. The organism, cell or tissue of claim 19, wherein the plant, plant cell or plant germ tissue is of the genus *cannabis*.

21. The organism or cell of claim 6, wherein the organism is an insect or the cell is an insect cell, optionally *Spodoptera frugiperda*.

22. A vector construct comprising a nucleic acid molecule comprising:

i) a nucleotide sequence encoding a polypeptide having the sequence set forth in SEQ ID NO: 2 or 6 or a polypeptide having at least 99.5% sequence identity to SEQ ID NO: 2 or 6 and encoding a polypeptide having cannabichromenic acid synthase activity;

ii) a nucleotide sequence having at least, greater than or about 99.5% sequence identity to SEQ ID NO: 1 or 5 and encoding a polypeptide having cannabichromenic acid synthase activity;

iii) a nucleotide sequence having at least, greater than or about 90% sequence identity to SEQ ID NO: 8 or 9 and encoding a polypeptide having cannabichromenic acid synthase activity; or iv) a nucleotide sequence that is the complement of i), ii) or iii).

23. The vector construct of claim 22, wherein the nucleotide sequence is as set forth in SEQ ID NO: 1 or 5 or a codon degenerate nucleotide sequence thereof, optionally wherein the codon degenerate nucleotide sequence comprises the sequence set forth in SEQ ID NO: 8 or 9, or the complement of any of the foregoing.

24. The vector construct of claim 22, wherein the encoded polypeptide has an amino acid sequence as set forth in SEQ ID NO: 2 or 6.

25. The vector construct of claim 22, wherein the nucleic acid molecule is conjugated to or comprises one or more heterologous moieties, optionally one or more of a heterologous nucleic acid, a detectable label or a tag.

26. The vector construct of claim 25, wherein the nucleic acid molecule encodes a polypeptide having the sequence set forth in SEQ ID NO: 6 or a polypeptide having at least 99.5% sequence identity to SEQ ID NO: 6 and the heterologous nucleic acid is a signal sequence, optionally alpha mating factor signal sequence, α-amylase signal sequence, glucoamylase signal sequence, serum albumin signal sequence, inulinase signal sequence, invertase signal sequence, killer protein signal sequence or lysozyme signal sequence.

27. A recombinant organism, cell or tissue comprising or produced using the vector construct of claim 22.

28. A composition comprising the vector construct of claim 22; and/or a purified extract of a recombinant cell, organism or tissue comprising or produced with said vector construct.

* * * * *

UNITED STATES PATENT AND TRADEMARK OFFICE
CERTIFICATE OF CORRECTION

| | | |
|---|---|---|
| PATENT NO. | : 10,724,009 B2 | Page 1 of 1 |
| APPLICATION NO. | : 16/443217 | |
| DATED | : July 28, 2020 | |
| INVENTOR(S) | : Jonathan E. Page and Jason M. Stout | |

It is certified that error appears in the above-identified patent and that said Letters Patent is hereby corrected as shown below:

In the Claims

Claim 1, Column 47, Line 51, delete "NO:_2 or 6" and insert --NO: 2 or 6--.

Claim 1, Column 47, Line 63, delete "complement of i), ii)." and insert --complement of i), ii) or iii)--.

Signed and Sealed this
Sixteenth Day of February, 2021

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 9

<210> SEQ ID NO 1
<211> LENGTH: 1635
<212> TYPE: DNA
<213> ORGANISM: Cannabis Sativa

<400> SEQUENCE: 1
atgaattgct caacattctc cttttggttt gtttgcaaaa taatattttt ctttctctca      60
ttcaatatcc aaatttcaat agctaatcct caagaaaact tccttaaatg cttctcggaa     120
tatattccta acaatccagc aaatccaaaa ttcatataca ctcaacacga ccaattgtat     180
atgtctgtcc tgaattcgac aatacaaaat cttagattca cctctgatac aaccccaaaa     240
ccactcgtta ttgtcactcc ttcaaatgtc tcccatatcc aggccagtat tctctgctcc     300
aagaaagttg gtttgcagat tcgaactcga agcggtggcc atgatgctga gggtttgtcc     360
tacatatctc aagtcccatt tgctatagta gacttgagaa acatgcatac ggtcaaagta     420
gatattcata gccaaactgc gtgggttgaa gccggagcta cccttggaga agtttattat     480
```

| | | |
|---|---|---|
| tggatcaatg agatgaatga gaattttagt tttcctggtg ggtattgccc tactgttggc | 540 | |
| gtaggtggac actttagtgg aggaggctat ggagcattga tgcgaaatta tggccttgcg | 600 | |
| gctgataata tcattgatgc acacttagtc aatgttgatg gaaaagttct agatcgaaaa | 660 | |
| tccatgggag aagatctatt ttgggctata cgtggtggag gaggagaaaa ctttggaatc | 720 | |
| attgcagcat gtaaaatcaa acttgttgtt gtcccatcaa aggctactat attcagtgtt | 780 | |
| aaaaagaaca tggagataca tgggcttgtc aagttattta caaatggcaa aatattgct | 840 | |
| tacaagtatg acaaagattt aatgctcacg actcacttca gaactaggaa tattacagat | 900 | |
| aatcatggga agaataagac tacagtacat ggttacttct cttccatttt tcttggtgga | 960 | |
| gtggatagtc tagttgactt gatgaacaag agctttcctg agttgggtat taaaaaaact | 1020 | |
| gattgcaaag aattgagctg gattgataca accatcttct acagtggtgt tgtaaattac | 1080 | |
| aacactgcta attttaaaaa ggaaattttg cttgatagat cagctgggaa gaagacggct | 1140 | |
| ttctcaatta agttagacta tgttaagaaa ctaatacctg aaactgcaat ggtcaaaatt | 1200 | |
| ttggaaaaat tatatgaaga gaggtagga gttgggatga tgtgttgta cccttacggt | 1260 | |
| ggtataatgg atgagatttc agaatcagca attccattcc ctcatcgagc tggaataatg | 1320 | |
| tatgaactt ggtacactgc tacctgggag aagcaagaag ataacgaaaa gcatataaac | 1380 | |
| tgggttcgaa gtgtttataa tttcacaact ccttatgtgt cccaaaatcc aagattggcg | 1440 | |
| tatctcaatt atagggacct tgatttagga aaaactaatc ctgagagtcc taataattac | 1500 | |
| acacaagcac gtatttgggg tgaaaagtat tttggtaaaa atttaacag gttagttaag | 1560 | |
| gtgaaaacca aagctgatcc caataatttt tttagaaacg aacaaagtat cccacctctt | 1620 | |
| ccaccgcgtc atcat | 1635 | |

<210> SEQ ID NO 2
<211> LENGTH: 545
<212> TYPE: PRT
<213> ORGANISM: Cannabis Sativa

<400> SEQUENCE: 2

```
Met Asn Cys Ser Thr Phe Ser Phe Trp Phe Val Cys Lys Ile Ile Phe
1               5                   10                  15

Phe Phe Leu Ser Phe Asn Ile Gln Ile Ser Ile Ala Asn Pro Gln Glu
                20                  25                  30

Asn Phe Leu Lys Cys Phe Ser Glu Tyr Ile Pro Asn Asn Pro Ala Asn
            35                  40                  45

Pro Lys Phe Ile Tyr Thr Gln His Asp Gln Leu Tyr Met Ser Val Leu
        50                  55                  60

Asn Ser Thr Ile Gln Asn Leu Arg Phe Thr Ser Asp Thr Thr Pro Lys
65                  70                  75                  80

Pro Leu Val Ile Val Thr Pro Ser Asn Val Ser His Ile Gln Ala Ser
                85                  90                  95

Ile Leu Cys Ser Lys Lys Val Gly Leu Gln Ile Arg Thr Arg Ser Gly
            100                 105                 110

Gly His Asp Ala Glu Gly Leu Ser Tyr Ile Ser Gln Val Pro Phe Ala
        115                 120                 125

Ile Val Asp Leu Arg Asn Met His Thr Val Lys Val Asp Ile His Ser
    130                 135                 140

Gln Thr Ala Trp Val Glu Ala Gly Ala Thr Leu Gly Glu Val Tyr Tyr
145                 150                 155                 160
```

```
Trp Ile Asn Glu Met Asn Glu Asn Phe Ser Phe Pro Gly Gly Tyr Cys
                165                 170                 175
Pro Thr Val Gly Val Gly Gly His Phe Ser Gly Gly Gly Tyr Gly Ala
            180                 185                 190
Leu Met Arg Asn Tyr Gly Leu Ala Ala Asp Asn Ile Ile Asp Ala His
        195                 200                 205
Leu Val Asn Val Asp Gly Lys Val Leu Asp Arg Lys Ser Met Gly Glu
    210                 215                 220
Asp Leu Phe Trp Ala Ile Arg Gly Gly Gly Glu Asn Phe Gly Ile
225                 230                 235                 240
Ile Ala Ala Cys Lys Ile Lys Leu Val Val Pro Ser Lys Ala Thr
                245                 250                 255
Ile Phe Ser Val Lys Lys Asn Met Glu Ile His Gly Leu Val Lys Leu
                260                 265                 270
Phe Asn Lys Trp Gln Asn Ile Ala Tyr Lys Tyr Asp Lys Asp Leu Met
            275                 280                 285
Leu Thr Thr His Phe Arg Thr Arg Asn Ile Thr Asp Asn His Gly Lys
        290                 295                 300
Asn Lys Thr Thr Val His Gly Tyr Phe Ser Ser Ile Phe Leu Gly Gly
305                 310                 315                 320
Val Asp Ser Leu Val Asp Leu Met Asn Lys Ser Phe Pro Glu Leu Gly
                325                 330                 335
Ile Lys Lys Thr Asp Cys Lys Glu Leu Ser Trp Ile Asp Thr Thr Ile
                340                 345                 350
Phe Tyr Ser Gly Val Val Asn Tyr Asn Thr Ala Asn Phe Lys Lys Glu
            355                 360                 365
Ile Leu Leu Asp Arg Ser Ala Gly Lys Lys Thr Ala Phe Ser Ile Lys
        370                 375                 380
Leu Asp Tyr Val Lys Lys Leu Ile Pro Glu Thr Ala Met Val Lys Ile
385                 390                 395                 400
Leu Glu Lys Leu Tyr Glu Glu Val Gly Val Gly Met Tyr Val Leu
                405                 410                 415
Tyr Pro Tyr Gly Gly Ile Met Asp Glu Ile Ser Glu Ser Ala Ile Pro
                420                 425                 430
Phe Pro His Arg Ala Gly Ile Met Tyr Glu Leu Trp Tyr Thr Ala Thr
            435                 440                 445
Trp Glu Lys Gln Glu Asp Asn Glu Lys His Ile Asn Trp Val Arg Ser
        450                 455                 460
Val Tyr Asn Phe Thr Thr Pro Tyr Val Ser Gln Asn Pro Arg Leu Ala
465                 470                 475                 480
Tyr Leu Asn Tyr Arg Asp Leu Asp Leu Gly Lys Thr Asn Pro Glu Ser
                485                 490                 495
Pro Asn Asn Tyr Thr Gln Ala Arg Ile Trp Gly Glu Lys Tyr Phe Gly
            500                 505                 510
Lys Asn Phe Asn Arg Leu Val Lys Val Lys Thr Lys Ala Asp Pro Asn
        515                 520                 525
Asn Phe Phe Arg Asn Glu Gln Ser Ile Pro Pro Leu Pro Pro Arg His
    530                 535                 540
His
545
```

```
<210> SEQ ID NO 3
<211> LENGTH: 30
<212> TYPE: DNA
<213> ORGANISM: Cannabis Sativa

<400> SEQUENCE: 3
ctgcaggaat gaattgctca acattctcct                                     30

<210> SEQ ID NO 4
<211> LENGTH: 37
<212> TYPE: DNA
<213> ORGANISM: Cannabis Sativa

<400> SEQUENCE: 4
aagctttcat ggtaccccat gatgacgcgg tggaaga                             37

<210> SEQ ID NO 5
<211> LENGTH: 1635
<212> TYPE: DNA
<213> ORGANISM: Artificial Sequence
<220> FEATURE:
<223> OTHER INFORMATION: Synthetic Construct
<220> FEATURE:
<221> NAME/KEY: misc_signal
<222> LOCATION: (4)..(84)
<223> OTHER INFORMATION: all or part of codons are present or absent

<400> SEQUENCE: 5
atgaattgct caacattctc cttttggttt gtttgcaaaa taatattttt ctttctctca    60
ttcaatatcc aaatttcaat agctaatcct caagaaaaact tccttaaatg cttctcggaa   120
tatattccta acaatccagc aaatccaaaa ttcatataca ctcaacacga ccaattgtat    180
atgtctgtcc tgaattcgac aatacaaaat cttagattca cctctgatac aaccccaaaa   240
ccactcgtta ttgtcactcc ttcaaatgtc tcccatatcc aggccagtat tctctgctcc    300
aagaaagttg gtttgcagat tcgaactcga agcggtggcc atgatgctga gggtttgtcc   360
tacatatctc aagtcccatt tgctatagta gacttgagaa acatgcatac ggtcaaagta    420
gatattcata gccaaactgc gtgggttgaa gccggagcta cccttggaga agtttattat    480
tggatcaatg agatgaatga aatttttagt tttcctggtg ggtattgccc tactgttggc    540
gtaggtggac actttagtgg aggaggctat ggagcattga tgcgaaatta tggccttgcg    600
gctgataata tcattgatgc acacttagtc aatgttgatg aaaagttct agatcgaaaa    660 tccatgggag aagatctatt tgggctata cgtggtggag gaggagaaaa ctttggaatc    720
attgcagcat gtaaaatcaa acttgttgtt gtcccatcaa aggctactat attcagtgtt   780
aaaaagaaca tggagataca tgggcttgtc aagttattta caaatgcgca aaatattgct    840
tacaagtatg acaaagattt aatgctcacg actcacttca gaactaggaa tattacagat   900
aatcatggga gaataagac tacagtacat ggttacttct cttccatttt tcttggtgga    960
gtggatagtc tagttgactt gatgaacaag agctttcctg agttgggtat aaaaaaaact   1020
gattgcaaag aattgagctg gattgataca accatcttct acagtggtgt tgtaaattac  1080
aacactgcta attttaaaaa ggaaattttg cttgatagat cagctgggaa gaagacggct  1140
ttctcaatta agttagacta tgttaagaaa ctaatacctg aaactgcaat ggtcaaaatt   1200
ttggaaaaat tatatgaaga gaggtagga gttgggatgt atgtgttgta cccttacggt    1260
ggtataatgg atgagatttc agaatcagca attccattcc ctcatcgagc tggaataatg  1320
tatgaacttt ggtacactgc tacctgggag aagcaagaag ataacgaaaa gcatataaac  1380
```

-continued

```
tgggttcgaa gtgtttataa tttcacaact ccttatgtgt cccaaaatcc aagattggcg    1440
tatctcaatt atagggacct tgatttagga aaaactaatc ctgagagtcc taataattac    1500
acacaagcac gtatttgggg tgaaaagtat tttggtaaaa attttaacag gttagttaag    1560
gtgaaaacca aagctgatcc caataatttt tttagaaacg aacaaagtat cccacctctt    1620
ccaccgcgtc atcat                                                     1635

<210> SEQ ID NO 6
<211> LENGTH: 545
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Asn or absent
<220> FEATURE:
<221> NAME/KEY: MISC_FEATURE
<222> LOCATION: (3)..(3)
<223> OTHER INFORMATION: Cys or absent
<220> FEATURE:
<221> NAME/KEY: MISC_FEATURE
<222> LOCATION: (4)..(4)
<223> OTHER INFORMATION: Ser or absent
<220> FEATURE:
<221> NAME/KEY: MISC_FEATURE
<222> LOCATION: (5)..(5)
<223> OTHER INFORMATION: Thr or absent
<220> FEATURE:
<221> NAME/KEY: MISC_FEATURE
<222> LOCATION: (6)..(6)
<223> OTHER INFORMATION: Phe or absent
<220> FEATURE:
<221> NAME/KEY: MISC_FEATURE
<222> LOCATION: (7)..(7)
<223> OTHER INFORMATION: Ser or absent
<220> FEATURE:
<221> NAME/KEY: MISC_FEATURE
<222> LOCATION: (8)..(8)
<223> OTHER INFORMATION: Phe or absent
<220> FEATURE:
<221> NAME/KEY: MISC_FEATURE
<222> LOCATION: (9)..(9)
<223> OTHER INFORMATION: Trp or absent
<220> FEATURE:
<221> NAME/KEY: MISC_FEATURE
<222> LOCATION: (10)..(10)
<223> OTHER INFORMATION: Phe or absent
<220> FEATURE:
<221> NAME/KEY: MISC_FEATURE
<222> LOCATION: (11)..(11)
<223> OTHER INFORMATION: Val or absent
<220> FEATURE:
<221> NAME/KEY: MISC_FEATURE
<222> LOCATION: (12)..(12)
<223> OTHER INFORMATION: Cys or absent
<220> FEATURE:
<221> NAME/KEY: MISC_FEATURE
<222> LOCATION: (13)..(13)
<223> OTHER INFORMATION: Lys or absent
<220> FEATURE:
<221> NAME/KEY: MISC_FEATURE
<222> LOCATION: (14)..(15)
<223> OTHER INFORMATION: Ile or absent
<220> FEATURE:
<221> NAME/KEY: MISC_FEATURE
<222> LOCATION: (16)..(18)
<223> OTHER INFORMATION: Phe or absent
<220> FEATURE:
<221> NAME/KEY: MISC_FEATURE
<222> LOCATION: (19)..(19)
<223> OTHER INFORMATION: Leu or absent
```

```
<220> FEATURE:
<221> NAME/KEY: MISC_FEATURE
<222> LOCATION: (20)..(20)
<223> OTHER INFORMATION: Ser or absent
<220> FEATURE:
<221> NAME/KEY: MISC_FEATURE
<222> LOCATION: (21)..(21)
<223> OTHER INFORMATION: Phe or absent
<220> FEATURE:
<221> NAME/KEY: MISC_FEATURE
<222> LOCATION: (22)..(22)
<223> OTHER INFORMATION: Asn or absent
<220> FEATURE:
<221> NAME/KEY: MISC_FEATURE
<222> LOCATION: (23)..(23)
<223> OTHER INFORMATION: Ile or absent
<220> FEATURE:
<221> NAME/KEY: MISC_FEATURE
<222> LOCATION: (24)..(24)
<223> OTHER INFORMATION: Glu or absent
<220> FEATURE:
<221> NAME/KEY: MISC_FEATURE
<222> LOCATION: (25)..(25)
<223> OTHER INFORMATION: Ile or absent
<220> FEATURE:
<221> NAME/KEY: MISC_FEATURE
<222> LOCATION: (26)..(26)
<223> OTHER INFORMATION: Ser or absent
<220> FEATURE:
<221> NAME/KEY: MISC_FEATURE
<222> LOCATION: (27)..(27)
<223> OTHER INFORMATION: Ile or absent
<220> FEATURE:
<221> NAME/KEY: MISC_FEATURE
<222> LOCATION: (28)..(28)
<223> OTHER INFORMATION: Ala or absent

<400> SEQUENCE: 6

Met Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Asn Pro Gln Glu
            20                  25                  30

Asn Phe Leu Lys Cys Phe Ser Glu Tyr Ile Pro Asn Asn Pro Ala Asn
        35                  40                  45

Pro Lys Phe Ile Tyr Thr Gln His Asp Gln Leu Tyr Met Ser Val Leu
    50                  55                  60

Asn Ser Thr Ile Gln Asn Leu Arg Phe Thr Ser Asp Thr Thr Pro Lys
65                  70                  75                  80

Pro Leu Val Ile Val Thr Pro Ser Asn Val Ser His Ile Gln Ala Ser
                85                  90                  95

Ile Leu Cys Ser Lys Lys Val Gly Leu Gln Ile Arg Thr Arg Ser Gly
            100                 105                 110

Gly His Asp Ala Glu Gly Leu Ser Tyr Ile Ser Gln Val Pro Phe Ala
        115                 120                 125

Ile Val Asp Leu Arg Asn Met His Thr Val Lys Val Asp Ile His Ser
    130                 135                 140

Gln Thr Ala Trp Val Glu Ala Gly Ala Thr Leu Gly Glu Val Tyr Tyr
145                 150                 155                 160

Trp Ile Asn Glu Met Asn Glu Asn Phe Ser Phe Pro Gly Gly Tyr Cys
                165                 170                 175

Pro Thr Val Gly Val Gly Gly His Phe Ser Gly Gly Gly Tyr Gly Ala
            180                 185                 190

Leu Met Arg Asn Tyr Gly Leu Ala Ala Asp Asn Ile Ile Asp Ala His
        195                 200                 205
```

```
Leu Val Asn Val Asp Gly Lys Val Leu Asp Arg Lys Ser Met Gly Glu
210                 215                 220

Asp Leu Phe Trp Ala Ile Arg Gly Gly Gly Glu Asn Phe Gly Ile
225                 230                 235                 240

Ile Ala Ala Cys Lys Ile Lys Leu Val Val Pro Ser Lys Ala Thr
                245                 250                 255

Ile Phe Ser Val Lys Lys Asn Met Glu Ile His Gly Leu Val Lys Leu
                260                 265                 270

Phe Asn Lys Trp Gln Asn Ile Ala Tyr Lys Tyr Asp Lys Asp Leu Met
            275                 280                 285

Leu Thr Thr His Phe Arg Thr Arg Asn Ile Thr Asp Asn His Gly Lys
290                 295                 300

Asn Lys Thr Thr Val His Gly Tyr Phe Ser Ile Phe Leu Gly Gly
305                 310                 315                 320

Val Asp Ser Leu Val Asp Leu Met Asn Lys Ser Phe Pro Glu Leu Gly
                325                 330                 335

Ile Lys Lys Thr Asp Cys Lys Glu Leu Ser Trp Ile Asp Thr Thr Ile
                340                 345                 350

Phe Tyr Ser Gly Val Val Asn Tyr Asn Thr Ala Asn Phe Lys Lys Glu
            355                 360                 365

Ile Leu Leu Asp Arg Ser Ala Gly Lys Lys Thr Ala Phe Ser Ile Lys
370                 375                 380

Leu Asp Tyr Val Lys Lys Leu Ile Pro Glu Thr Ala Met Val Lys Ile
385                 390                 395                 400

Leu Glu Lys Leu Tyr Glu Glu Val Gly Val Gly Met Tyr Val Leu
                405                 410                 415

Tyr Pro Tyr Gly Gly Ile Met Asp Glu Ile Ser Glu Ser Ala Ile Pro
            420                 425                 430

Phe Pro His Arg Ala Gly Ile Met Tyr Glu Leu Trp Tyr Thr Ala Thr
            435                 440                 445

Trp Glu Lys Gln Glu Asp Asn Glu Lys His Ile Asn Trp Val Arg Ser
            450                 455                 460

Val Tyr Asn Phe Thr Thr Pro Tyr Val Ser Gln Asn Pro Arg Leu Ala
465                 470                 475                 480

Tyr Leu Asn Tyr Arg Asp Leu Asp Leu Gly Lys Thr Asn Pro Glu Ser
                485                 490                 495

Pro Asn Asn Tyr Thr Gln Ala Arg Ile Trp Gly Glu Lys Tyr Phe Gly
            500                 505                 510

Lys Asn Phe Asn Arg Leu Val Lys Val Lys Thr Lys Ala Asp Pro Asn
            515                 520                 525

Asn Phe Phe Arg Asn Glu Gln Ser Ile Pro Pro Leu Pro Pro Arg His
            530                 535                 540

His
545

<210> SEQ ID NO 7
<211> LENGTH: 28
<212> TYPE: PRT
<213> ORGANISM: Cannabis Sativa

<400> SEQUENCE: 7

Met Asn Cys Ser Thr Phe Ser Phe Trp Phe Val Cys Lys Ile Ile Phe
1               5                   10                  15

Phe Phe Leu Ser Phe Asn Ile Gln Ile Ser Ile Ala
                20                  25
```

<210> SEQ ID NO 8
<211> LENGTH: 1635
<212> TYPE: DNA
<213> ORGANISM: Artificial Sequence
<220> FEATURE:
<223> OTHER INFORMATION: Synthetic Construct

<400> SEQUENCE: 8

| | | |
|---|---|---|
| atgaactgct cgacatttag tttttggttt gtgtgcaaga tcattttttt ttttctttcg | 60 |
| tttaacattc agattagtat tgcaaacccg caggagaact ttctcaaatg ttttagcgaa | 120 |
| tatatcccga caacccggc caacccgaaa ttcatttaca cacaacacga tcaactgtac | 180 |
| atgagcgtat tgaacagcac catccagaat ttgcgcttta cttcggacac aacgccgaag | 240 |
| cctctggtca tcgttacgcc ctcgaatgtt tcacatatcc aagcgtcaat tctttgttct | 300 |
| aaaaaggtcg gcctgcagat tcgcacacg tcggcggcc atgatgccga aggtctgtct | 360 |
| tacatctcac aagtcccttt cgcaatcgtt gatttgcgga acatgcacac tgtaaaagtt | 420 |
| gatattcact cacaaaccgc ttgggtcgaa gcaggtgcca cgcttgggga agtatattac | 480 |
| tggattaacg aaatgaacga gaatttctcg tttccaggcg gttactgccc aaccgtaggt | 540 |
| gtgggcggtc attttttccgg aggcggttat ggtgcgttaa tgcgcaacta tggcctggcg | 600 |
| gcagacaata ttattgatgc ccacctcgtt aatgtggatg gtaaagtact ggatcgcaaa | 660 |
| tcaatgggtg aagacctctt ctgggcgatt cgtggtgggg gtggcgagaa ctttggtatc | 720 |
| atcgcggcat gtaagatcaa gctggtggta gttccgtcta aagcgaccat ctttagcgtg | 780 |
| aaaaaaaaca tggagattca cggcctggta aaattgttca caaatggca gaacatcgct | 840 |
| tacaaatacg acaaagatct gatgttaacg actcacttcc gcacccgtaa cattactgac | 900 |
| aatcacggca aaaataagac tactgtgcat ggttacttta gtagtatctt cctgggtgga | 960 |
| gtcgattccc tggtcgattt aatgaacaag agctttccgg agctggggat taaaaaaacc | 1020 |
| gactgtaaag agctgagttg gatcgacacg acgatcttct acagcggagt agtcaactac | 1080 |
| aacactgcca actttaagaa agaaattctg ctggaccgca gcgcaggtaa aaagaccgcc | 1140 |
| ttctccatca aactggatta cgtcaaaaag ctgattccgg aaacagcaat ggtaaagatt | 1200 |
| ctggaaaaac tgtatgaaga gaggttggc gttggcatgt atgtcttata ccgtatgggg | 1260 |
| ggcattatgg atgaaatttc tgaaagtgct attcccttcc cacaccgcgc ggggattatg | 1320 |
| tacgaactgt ggtatacggc cacgtgggaa aaacaagagg acaatgagaa acacatcaac | 1380 |
| tggggttcggt cagtatataa ctttaccacc ccgtatgtct cgcagaaccc gcgtctggcg | 1440 |
| tatctgaact atcgcgatct tgatttgggt aaaaccaatc cggaaagccc gaataactac | 1500 |
| acccaggcac gcatttgggg ggaaaaatat tcgggaaaa acttcaaccg gctggtgaag | 1560 |
| gtgaaaacga aggctgaccc gaataacttt tttcggaatg aacaaagcat tccgccgtta | 1620 |
| ccgccgcgcc accac | 1635 |

<210> SEQ ID NO 9
<211> LENGTH: 1635
<212> TYPE: DNA
<213> ORGANISM: Artificial Sequence
<220> FEATURE:
<223> OTHER INFORMATION: Synthetic Construct

<400> SEQUENCE: 9

| | | |
|---|---|---|
| atgaattgta gtactttctc tttctggttt gtttgtaaga ttatattttt ttttcttagt | 60 |
| ttcaatatac aaatttcaat tgcaacccct caagaaaatt tccttaagtg cttttcagaa | 120 |

```
tatatcccta ataatcctgc aaaccctaaa ttcatttata cacaacatga tcagttatat    180
atgtctgtct taaactctac cattcaaaat ttgaggttca cgtctgatac aaccccaaag    240
cctttagtta tcgtgacacc ctctaacgtt agtcatattc aggctagtat cttatgttca    300
aaaaaagtgg gtttacaaat cagaactagg tctggtggtc atgacgcgga aggtctgtct    360
tacatatctc aggtgccgtt tgcaatcgtt gatctacgta atatgcatac agttaaagtc    420
gatattcact ctcaaactgc atgggtcgag gctggtgcca ctctaggtga agtttattac    480
tggatcaatg aaatgaacga gaattttttcc ttcccaggtg gttattgtcc tactgtgggt    540
gtaggcggac acttttctgg cgggggtat ggtgctttga tgaggaacta tggtttggcc     600
gccgataata taattgacgc ccatcttgta aacgtcgacg ggaaggttct ggaccgtaaa    660
tctatgggtg aagatttatt ctgggcgata agaggtggcg ggggagagaa ctttggtatt    720
atcgcagctt gtaagattaa gttagttgtt gtccctcaa aagcaacaat tttttcagtg     780
aagaagaaca tggaaatcca cggtttggta aaactgttta ataaatggca gaatattgcc    840
tacaaatacg ataaggattt gatgttgaca acacatttca gaactagaaa tattactgac    900
aaccacggaa agaacaagac aaccgtccat ggatatttta gttctatttt cttaggcgga    960
gttgattcac tagtagactt aatgaacaag tctttcccg aattgggaat aaaaaaaacc    1020
gattgcaagg aattatcctg gatagataca acaatattct actctggagt cgttaattat   1080
aatacggcca actttaagaa ggaaatatta ttagatcgtt ccgcaggtaa aaagacagct   1140
ttttccataa aattggacta cgtcaaaaaa ttaattcctg agacagccat ggtaaaaata   1200
ttggaaaaat tgtacgaaga ggaggtaggc gtgggtatgt atgtgttata cccatacggt   1260
ggtattatgg atgaaatttc tgagagcgct attcccttcc cccatcgtgc aggtataatg   1320
tatgaattat ggtacacagc aacatgggaa aaacaagagg ataacgaaaa gcatattaat   1380
tgggtacgta gtgtgtacaa ctttacgaca ccttacgtgt cccaaaatcc aagattagcg   1440
tatttgaact atagagactt agatttaggt aaaacaaacc ctgagtctcc aaataattac    1500
acccaagcca ggatttgggg tgaaaaatac ttcggcaaaa atttcaatag attggttaag    1560
gtaaaaacta aggcggatcc aaacaatttt tttagaaatg agcagagtat tccgcccctg    1620
cctccaagac accat                                                   1635
```